US006806354B2

(12) United States Patent
Schroit

(10) Patent No.: US 6,806,354 B2
(45) Date of Patent: Oct. 19, 2004

(54) METHODS AND COMPOSITIONS FOR INDUCING AUTOIMMUNITY IN THE TREATMENT OF CANCERS

(75) Inventor: Alan J. Schroit, Houston, TX (US)

(73) Assignee: Board of Regents University of Texas System, Austin, TX (US)

( * ) Notice: Subject to any disclaimer, the term of this patent is extended or adjusted under 35 U.S.C. 154(b) by 0 days.

(21) Appl. No.: 09/974,753

(22) Filed: Oct. 9, 2001

(65) Prior Publication Data

US 2003/0004097 A1 Jan. 2, 2003

Related U.S. Application Data

(62) Division of application No. 09/224,558, filed on Dec. 30, 1998, now Pat. No. 6,300,308.
(60) Provisional application No. 60/071,794, filed on Dec. 31, 1997.

(51) Int. Cl.$^7$ .......................... C07K 16/00; A61K 45/00

(52) U.S. Cl. ............................... 530/387.1; 530/388.1; 424/283.1

(58) Field of Search .......................... 530/387.1, 388.1, 530/387.5; 424/283.1, 130.1

(56) References Cited

U.S. PATENT DOCUMENTS

| 4,196,265 A | 4/1980 | Koprowski et al. ....... 435/70.21 |
| 4,916,118 A | 4/1990 | Fidler et al. .................. 514/16 |
| 4,916,448 A | 4/1990 | Thor .......................... 340/970 |
| 4,994,440 A | 2/1991 | Creaven ........................ 514/8 |
| 6,312,694 B1 | 11/2001 | Thorpe et al. ............ 424/178.1 |

FOREIGN PATENT DOCUMENTS

JP           3197865         8/1981

OTHER PUBLICATIONS

Tamamura et al. (Japan. J. Exp. Med. vol. 41, 1 pp. 31–38, 1971).*
"New cancer metastasis inhibitory compsn. for both humans and animals—comprises peptide cpds. having cell adhesive activity and lipid(s) having 14–24C fatty acid residue, sphingoglycolipid and cholesterol residues," abstract of JP08225457, Derwent Publications Ltd., #AN 96–450927, 1996.
"Remington's Pharmaceutical Sciences" 15 Edition, pp. 1035–1038 and 1570 and 1580.
Allen and Choun, "Large unilamellar liposomes with low uptake into the reticuloendothelial system," *FEBS Lett.,* 223:42–46, 1987.
Alving, "Antibodies to liposomes, phospholipids and phosphate esters," *Chem. Phys. Lipids,* 40:303–314, 1986.
Asherson and Cervera, "Antiphospholipid Syndrome," *J. Invest. Dermatol.,* 100((1):21S–27S, 1993.
Balasubramanian and Schroit, "Characterization of Phosphatidylserine–dependent $\beta_2$ –Glycoprotein I Macrophage Interactions," *J. Biol. Chem.,* 273(44), pgs. 29272–29277, 1998.
Baldwin et al., "Surface exposure of phosphatidylserine is associated with the swelling and osmotically–induced fusion of human erythrocytes in the presence of $Ca^{2+}$," *Biochim. Biophys. Acta,* 1028:14–20, 1990.
Balet et al., "1–Palmitoyl–2–thiopalmitoyl phosphatidylcholine, a highly specific chromogenic substrate of phosphol ipase $A_2$," *Biochem. Biophys. Res. Commun.,* 150:561–567, 1988.
Banerji and Alving, "Antibodies to liposomal phosphatidylserine and phosphatidic acid," *Biochem. Cell. Biol.,* 68:96–101, 1990.
Bate et al., "Phospholipids coupled to a carrier induce IgG antibody that blocks tumour necrosis factor induction by toxic malaria antigens," *Immunol.,* 79:138–145, 1993.
Becker et al., "Antiphospholipid syndrome associated with immunotherapy for patients with melanoma," *Cancer,* 73:1621–1624, 1994.
Bennett et al., "Binding and phagocytosis of apoptotic vascular smooth muscle cells is mediated in part by exposure of phosphatidylserine," *Circ. Res.,* 77:1136–1142, 1995.
Bevers et al., "Changes in membrane phospholipid distribution during platelet activation," *Biochim. Biophys. Acta,* 736:57–66, 1983.
Bevers et al., "Defective Ca2+–induced microvesiculation and deficient expression of procoagulant activity in erythrocytes from a patient with a bleeding disorder: astudy of the red blood cells of scott syndrome," *Blood,* 79:380–388, 1992.
Bevers et al., "Generation of Prothrombin–converting activity and the exposure of phosphatidylserine at the outer surface of platelets," *Eur. J. Blochem.,* 122:429–436, 1982.
Bruckheimer and Schroit, "Membrane phospholipid asymmetry: host response to the externalization of phosphatidylsrine," *J. Leukocyte Biol.,* 59:784–788, 1996.
Brunner and Richards, "Analysis of membranes photolabeled with lipid analogues," *J. Biol. Chem.,* 255:3319–3329, 1980.
Comfurius et al., "Enzymatic synthesis of phosphatidylserine on small scale by use of a one–phase system," *J. Lipid Res.,* 31:1719–1721, 1990.

(List continued on next page.)

*Primary Examiner*—Gary B. Nickol
(74) *Attorney, Agent, or Firm*—Fulbright & Jaworski L.L.P.

(57) ABSTRACT

Disclosed are methods and compositions for the prevention and treatment of cancers using lipid-carrier protein conjugate compositions for generating lipid-specific immune responses in an animal. Also disclosed are methods for making phosphatidylserine conjugate compositions and their formulation for use in a variety of pharmaceutical applications including the detection and treatment of a variety of cancers and related conditions.

20 Claims, 7 Drawing Sheets

OTHER PUBLICATIONS

Figure 1:
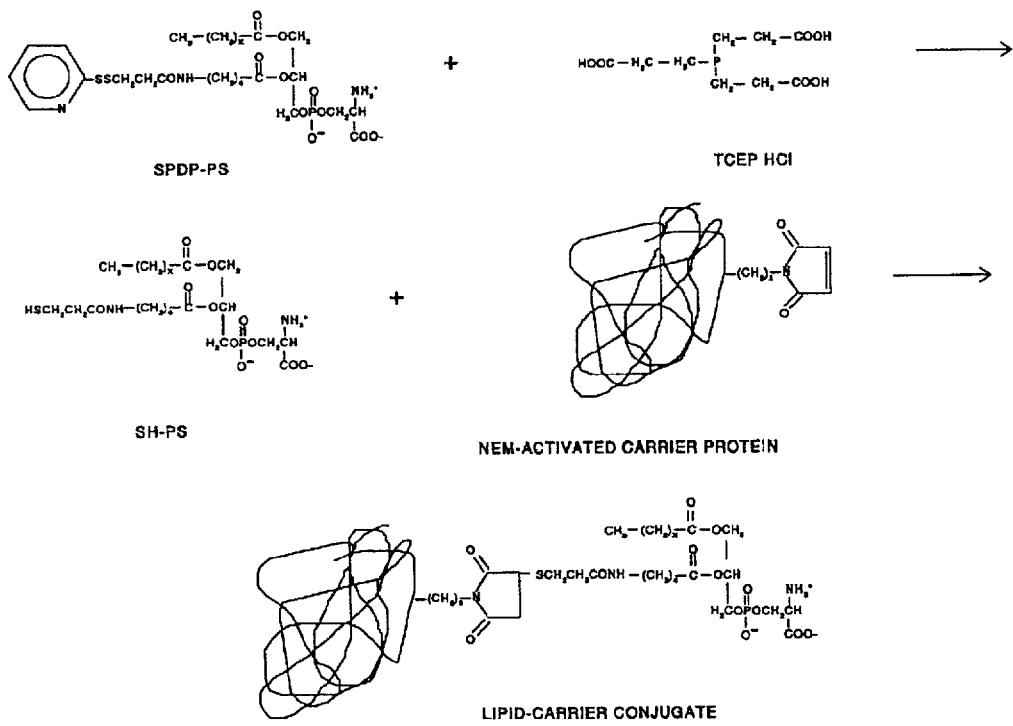

Connor et al., "Differentiation–dependent expression of phosphatidylserine in mammalian plasma membranes: Quantitative assessment of outer–leaflet lipid by prothrombinase complex formation," *Proc. Natl. Acad. Sci. USA,* 86:3184, 1989.
Connor et al., Exposure of phosphatidylserine in the outer leaflet of human red blood cell*J. Biol. Chem.,* 269:2399–2404, 1994.
Couvreur et al., "Nanocapsules: a new type of lysosomotropic carrier," *FEBS Lett.,* 84:323–326, 1977.
Couvreur, "Polyalkylcyanoacrylates as colloidal drug cariers," *Crit. Rev. Ther. Drug Carrier Syst.,* 5:1–20, 1988.
Creaven et al., "Initial Clinical Trial of Muramyl Tripeptide Derivative (MTP–PE) Encapsulated in Lipsomes: an Interim Report," *UCLA Symp. Mol. Cell. Bol.,* New Ser 89:297–303, 1989, Abstract Only.
Devaux and Zachowski, "Maintenance and consequences of membrane phospholipid asymmetry," *Chem. Phys. Lipids,* 73:107, 1994.
Devaux, "Static and cynamic lipid asymmetry in cell membranes," *Biochemistry,* 30:1163–1173, 1991.
Diaz et al., "Generation of phenotypically aged phosphatidylserine–expressing erythrocytes by dialauroylphosphatidylcholine–induced vesiculation," *Blood,* 87:2956–2961, 1996.
Diaz et al., "Synthesis of disulfide–containing phospholipid analogs for the preparation of head group–specific lipid antigens: generation of phosphatidylserine antibodies," *Bioconjugate Chem.,* 9:250–254, 1988.
Etemadi, "Membrane asymmetry, a survey and critical appraisal of the methodology, II. methods for assessing the unequal distribution of lipids," *Biochim. Biophys. Acta,* 604:423–475, 1980.
Fadok et al., "Exposure of phosphatidylserine on the surface of apoptotic lymphocytes triggers specific recognition and removal by macrophages," *J. Immunol.,* 148:2207–2216, 1992.
Gabizon and Papahadjopoulos, "Liposome formulations with prolonged circulation time in blood and enhance uptake by tumors," *Proc. Natl. Acad. Sci. USA,* 85:6949–6953, 1988.
Gaffet et al., Phosphatidylserine exposure on the platelet plasma membrane during A23187–induced activation is independent of cytoskeleton reorganization, *Eur. J. Cell Biol.,* 67:336–345, 1995.
Galli et al., "Anticardiolipin antibodies (ACA) directed not to cardiolipin but to a plasma protein cofactor," *Lancet,* 335:1544–1547, 1990.
Gefter et al., "Simple method for polyethylene glycol–promoted hybridization of mouse myeloma cells," *Somat. Cell Genet.,* 3:231–236, 1977.
Geldwerth et al., "Transbilayer mobility and distribution of red cell phospholipids during storage," *J. Clin. Invest.,* 92:308–314, 1993.
Ghosh and Bachhawat, "Targeting of Liposomes to Hepatocytes," *Targeted Diagn. Ther.,* 4:87–103, 1991.
Goding, "Monoclonal Antibodies: Principles and Practice," pp. 60–74. 2nd Edition, Academic Press, Orlando, FL, 1986.
Gordesky et al, "The reaction of chemical probes iwth the erythrocyte membrane," *J. Membr. Biol.,* 20:111–132, 1975.
Grassetti and Murray, "Determination of sulfhydryl groups with 2,2'– or 4,4'–dithiodipyridine," *Arch. Biochem. Biophys.,* 119:41–49, 1967.

Gupta et al., "Adjuvants for human vaccines—current status, problems and future prospects," *Vaccine,* 13(14):1263–1267, 1995.
Henry–Michelland et al., "Attachment of antibiotics to nanoparticles: preparation, drug–release and antimicrobial activity in vitro," *Int. J. Pharm.,* 35:121–127, 1987.
Herrmann and Devaux, "Alteration of the aminophospholipid translocase activity during in vivo and artifical aging of human erythrocytes," *Biochim. Biophys. Acta,* 1027:41–46, 1990.
Herstoff and Bogaars, "Cutaneous lupus erythematosus associated with melanoma and BCG vaccine therapy,"*Arch. Dermatol.,* 115(7):856–859, 1979.
Janeway et al.,*Immunobiology,* Garland Publishing, p. 1:32, 1994.
Jue et al., "Addition of sulfhydryl groups to *Escherichia coli* ribosomes by protein modification with 2–iminothiolane (methyl 4–mercaptobutyrimidate)," Biochemistry, 17:5399–5405, 1978.
Katsuragawa et al., "Monoclonal antiphosphatidylserine antibody reactivity against human first–trimester placental trophoblasts," *Am. J. Obstetr. Gynecol.,* 172:1592–1597, 1995.
Killion and Baker, "Autoreactive factors identify tumorhost heterogeneity and responsiveness to immunotherapy," *Cancer Immunol Immunother.,* 12:111–117, 1982.
Kohler and Milstein, "Derivation of specific antibody–producing tissue culture and tumor lines by cell fusion," *Eur. J. Immunol.,* 6:511–519, 1976.
Kuypers et al., "Detection of altered membrane phospholipid asymmetry in subpopulations of human red blood cells using fluorescently labeled annexin V," *Blood,* 87:1179–1187, 1996.
Mackworth–Young, "Antiphospholipid antibodes: more than just a disease marker?," *Immunol. Today,* 11(2):60–65, 1990.
Maneta–Peyret et al., "Demonstration of high specificity antibodies against phosphatidylserine," *J. Immun. Met.,* 108:123–127, 1988.
Maneta–Peyret et al., "Demonstration that anti–phospholipid auto–antibodies react with both anionic d zwitterionic phospholipids," *Immunol. Lett.,* 35:141–146, 1993.
Maneta–Peyret et al., "Specific immunocytochemical visualization of phyosphatidylserine," *J. Immunol. Meth.,* 122:155–159, 1989.
McNeil et al., "Anti–phospholipid antibodies are directed against a complex antigen that includes a lipid–binding inhibitor of coagulation: $\beta_2$–glycoprotein I (apolipoprotein H)," *Proc. Natl. Acad. Sci. USA,* 87:4120–4124, 1990.
Menon, "Flippases," *Trends Cell Biol.,* 5:355, 1995.
Mizushima and Igarashi, "Studies on polypeptide drug delivery systems: tissue distribution of immunoglobulin G conjugated with lecithin," *J. of Controlled Release,* 17:99–104, 1991.
Moestrup et al., "$\beta_2$–Glycoprotein–I (Apolipoprotein H) and $\beta_2$–Glycoprotein–I–Phospholipid Complex Harbor a Recognition Site for the Endocytic Receptor Megalin," *J. Clin. Invest.,* 102(5), pgs. 902–909, 1998.
Naldi et al, "Antiphospholipid antibodies and melanoma: a link?," *Dermatology,* 184(2):156, 1992.
Nelson, "Autoantibodies in cancer patients," *Pathology,* 9(2):155–160, 1977.

Oosting et al., "Antiphospholipid antibodies directed against a combination of phospholipids with prothrombin, protein c, or protien s: an explanation for their pathogenic mechanism," *Blood,* 81:2618–2625, 1993.

Pierotti and Colnaghi, "Natural antibodies directed against murine lymphosarcoma cells," *J. Natl. Cancer Inst.,* 55(4):945–949, 1975.

Poltz and Kostner, "The binding of $\beta_2$glycoprotein–I to human serum lipoprotiens," *FEBS Lett.,* 102:183–186, 1979.

Rauch and Janoff, "Phospholipid in the hexagonal II phase is immunogenic: evidence for immunorecognition of non-bilayer lipid phases in vivo," Proc. *Natl. Acad. Sci. USA,* 87:4112–4114, 1990.

Rauch et al., "Human hybridoma lupus anticoagulants distinguish between lamellar and hexagonal phase lipid systems," *J. Biol. Chem.,* 262:9672–9677, 1986.

Regen, "Polymerized–depolymerized vesicles. A reversible phosphatidylcholine–based membrane," *J. Am. Chem. Soc.,* 105:6354–6355, 1983.

Riddles et al., "Reassessment of ellman's reagent," *Meth. Enzymol.,* 91:49–60, 1983.

Rosenberg and Rogentine, "Natural human antibodies to "hidden" membrane components," *Nature,* 239:203, 1972.

Rosing et al., "The role of activated human platelets in prothrombin and factor x activation," *Blood,* 65:319–322, 1985.

Rosing et al., "The role of phospholipids and factor $V_a$ in the prothrombinase complex," *J. Biol. Chem.,* 255:274–283, 1980.

Rote et al., "Expression of phosphatidylserine–dependent antigens on teh surface of differentiating BeWo human choriocarcinoma cells," *Am. J. Rep. Immunol.,* 33:114–121, 1995.

Rote et al., Immunologic detection of phosphatidylserine externalization during thrombin–induced platelet activation- *Clin. Immunol. Immunopathol.,* 66:193–200, 1993.

Roubey, "Autoantibodies to phospholipid–binding plasma proteins: a new view of lupus anticoagulants and other "antiphospholipid" autoantibodies," *Blood,* 84:2854–2867, 1994.

Sambrano and Steinberg, "Recognition of oxidatively damaged and apoptotic cells by an oxidized low density lipoprotien receptor on mouse peritoneal macrophages: role of membrane phosphatidylserine," *Proc. Natl. Acad. Sci. USA,* 92:1396–1400, 1995.

Samuel et al., "Polymerized–deploymerized vesicles. Reversible thiol–disulfide–based phosphatidylcholine membranse," *J. Am. Chem. Soc.,* 107:42–47, 1985.

Schick et al, "Location of phosphatidylethanolamine and phosphatidlyserine in the human platelet plasma membrane," *J. Clin. Invest.,* 57:1221–1226, 1976.

Schousboe, "Purification, characterization and identification of an agglutinin in human serum," *Biochim. Biophsy. Acta,* 579:396–408, 1979.

Schroit and Madsen, "Synthesis and properties of radioiodinated phosphloipid analogues that spontaneously undergo vesicle–vesicle and vesicle–cell transfer," *Biochemistry,* 22:3617–3623, 1983.

Schroit and Zwall, "Transbilayer movement of phospholipids in red cell and platelet membranes," *Biochim. Biophys. Acta,* 1071:313–329, 1991.

Sims et al., Assembly of the platelet prothrombinase complex is linked to vesiculation of the platelet plasma membrane, *J. Biol. Chem.,* 264:17049–17057, 1989.

Tait and Gibson, "Measurement of membrane phospholipid asymmetry in normal and sickle–cell erythrocytes by means of annexin V binding," *J. Lab. Clin. Med.,* 123:741–748, 1994.

Tamamura et al., "The immunological relations between acidic phospholipids and their antibodies," *Jpn. J. Exp. Med.,* 41:31–38, 1971.

Tannock et al., *The Basic Science of Oncology,* $2^{nd}$ Edition, p. 247, $1^{st}$ column, 1992.

Thiagarajan and Tait, "Binding of annexin V/Placental anticoagulant protein I to platelets," *J. Biol. Chem.,* 265:17420–17423, 1990.

Umeda, "Effective production of monoclonal antibodies against phosphatidylserine: stereo–specific recognition of phosphatidylserine by monoclonal antibody,", *Immunol.,* 143:2273–2279, 1989.

Utsugi et al., "Elevated expression of phosphatidylserine in the outer membrane leaflet of human tumor cells and recognition by activated human blood monocytes," *Cancer Res.,* 51(11):3062–3066, 1991.

Van Dieijen et al., "The role of phospholipid and factor $VIII_a$ in the activation of bovine factor x," *J. Biol. Chem.,* 256:3433–3442, 1981.

Verhoven et al., "Mechanisms of phosphatidylserine exposure, a phagocyte recognition signal, on apoptotic t lymphocytes," *J. Exp. Med.,* 182:1597–1601, 1995.

Verkleij et al., "The asymmetric distribution of phospholipids in the human red cell membrane, a combined study using phospholipases and freeze–etch electron microscopy," *Biochim. Biophys. Acta,* 323(2):178–193, 1974.

Vermes et al., "A novel assay for apoptosis flow cytometric detection of phosphatidylserine expression on early apoptotic cells using fluorescein labelled annexin V," *J. Immunol. Meth.,* 184:39–51, 1995.

Wurm, "$\beta_2$–glycoprotein–I (apolipoprotein h) interactions with phospholipid vesicles," *Int. J. Biochem.,* 16:511–515, 1984.

Zwaal and Schroit, "Pathophysiologic implications of membrane phospholipid asymmetry in blood cells," *Blood,* 89:1121–1132, 1997.

Zwaal et al.,"Organization of phospholipids in human red cell membranes as detected by the action of various purified phospholipases," *Biochim. Biophsy. Acta,* 406(1):83–96, 1975.

* cited by examiner

FIG. 6A
FIG. 6C
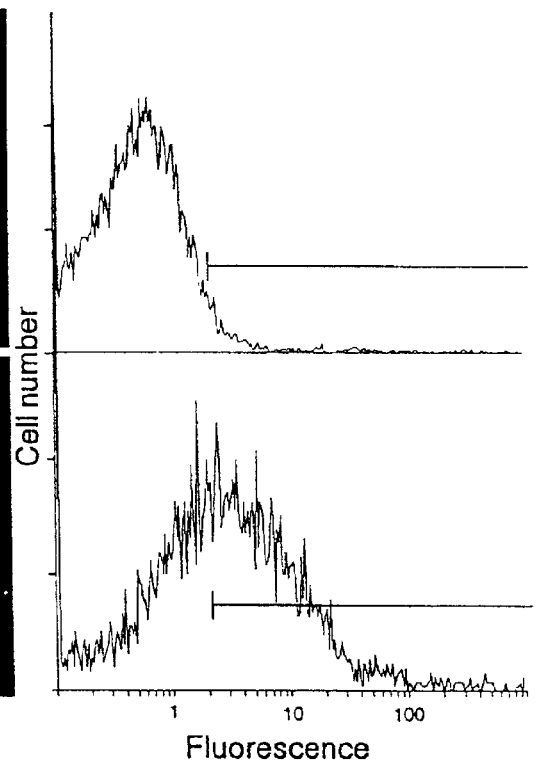
FIG. 6B
FIG. 6D

METHODS AND COMPOSITIONS FOR INDUCING AUTOIMMUNITY IN THE TREATMENT OF CANCERS

This application is a division of Ser. No. 09/224,558 filed Dec. 30, 1998 now U.S. Pat. No. 6,300,308.

The present application is a continuation-in-part of U.S. Provisional Patent Application Serial No. 60/071,794 filed Dec. 31, 1997. The entire text of the above-referenced disclosure is specifically incorporated by reference herein without disclaimer.

The United States has certain rights in the present invention pursuant to Grant DK41714 from the National Institutes of Health.

1.0 BACKGROUND OF THE INVENTION

1.1 Field of the Invention

The present invention relates generally to the field of oncology. More particularly, certain embodiments concern methods for making and using lipid-carrier protein conjugate compositions such as phosphatidylserine (PS)-conjugates for generating lipid-specific immune responses in an animal. Also disclosed are methods for making PS antigen and antibody compositions and their use in a variety of therapeutic applications, including the formulation of pharmaceutical compositions for the prevention and treatment of cancers.

1.2 Description of the Related Art

The results of many studies have led to the concept that membrane phospholipid asymmetry is ubiquitous. The outer leaflet of eukaryotic plasma membranes contains most of the cholinephospholipids, whereas the aminophospholipids are mainly present in the cell's inner leaflet (Devaux, 1991; Schroit and Zwaal, 1991). While asymmetry seems to be the rule for normal cells, loss of membrane lipid sidedness, in particular the emergence of phosphatidylserine (PS) at the cell surface, results in the expression of altered surface properties that modulates cell function and influences the cells interaction with its environment (Zwaal and Schroit, 1997). For example, the exposure of PS promotes coagulation and thrombosis by platelets (Bevers et al., 1983; Rosing et al., 1985; Thiagarajan and Tait, 1990) and the recognition of apoptotic (Fadok et al., 1992; Bennett et al., 1995; Sambrano and Steinberg, 1995; Verhoven et al., 1995) and aged (Herrmann and Devaux, 1990; Geldwerth et al., 1993; Connor et al. 1994) cells by the reticuloendothelial system.

To characterize these and other PS-related processes, new tools are required to determine physiologically-dependent alterations in the distribution of PS in cell membranes. Although the application of classical biochemical methodologies (Gordesky et al., 1975; Schick et al., 1976; Etemadi, 1980; Bevers et al., 1982) has yielded important information on PS asymmetry, most of these methods are invasive and destructive. Recently developed methods, such as the PS-dependent prothrombinase assay (Bevers et al., 1983; Rosing et al., 1980; Van Dieijen et al., 1981) and labeled annexin V binding (Thiagarajan and Tait, 1990; Tait and Gibson, 199,4; Vermes et al., 1995; Kuypers et al., 1996), are non-invasive and have provided the means to assess the presence and topology of PS in the outer leaflet of viable cells. These methods, however, require the inclusion of various plasma cofactors and/or divalent cations which might influence the lateral distribution of lipids in the plane of the membrane.

While antibodies against different membrane components has become an indispensable aid in the study of membrane structure and function, little attention has been given to the application of lipid-specific antibodies for studying lipid-dependent processes. Because of the inherent difficulty of producing antibodies against small highly conserved lipids, the development of lipid antibodies has progressed slowly. Nonetheless, several laboratories have produced antibodies against certain phospholipid species by immunization with liposomes (Maneta-Peyret et al., 1988; Maneta-Peyret et al., 1989; Banedi and Alving, 1990) or by adsorption of monomeric phospholipids to proteins (Maneta-Peyret et al., 1989; Tamamura et al., 1971), bacteria (Umeda et al., 1989) and acrylamide (Maneta-Peyret et al., 1988; Maneta-Peyret et al., 1989). Antibodies produced by these methods, however, may cross-react with different lipids (Banedi and Alving, 1990; Umeda et al., 1989) and other phosphate-containing moieties (Alving, 1986).

1.3 Deficiencies in the Prior Art

While some methods have been developed in these areas, what is lacking in the prior art are effective methodologies for generating immune responses that are useful in various treatment regimens, including those specific for oncology.

Several reports on the production of PS antibodies have been published. These include unrelated methods and approaches using PS-containing liposomes (Banedji and Alving, 1990), PS-coated Salmonella (Umeda et at., 1989) and acrylamide-entrapped PS (Maneta-Peyret et al., 1988). There is one report concerning carrier (KLH)-coupled PS (Bate et al., 1993). However, the chemistry employed to make the conjugate couples lipid to the protein carrier via the lipids primary amine thereby destroying antigenic specificity. Immunization with this conjugate produced antibody activity which inhibited the production of tumor necrosis factor by malaria-infected erythrocytes. Whether the antibodies had any lipid specificity was not investigated. This is unlikely, however, considering that the conjugation chemistry destroyed the key primary amine determinant of phosphatidylserine. Thus, there exists an immediate need for an effective method of producing highly-specific anti-PS antibodies and cell-mediated PS responses for use in the diagnosis and treatment of various cancers and related conditions.

2.0 SUMMARY OF THE INVENTION

The present invention overcomes one or more of these and other drawbacks inherent in the prior art by providing novel compositions and methods for their use in the induction of an autoimmune response to lipids such as PS. Disclosed are methods for the preparation and use of novel lipid antigen compositions which generate an immune response in an animal. Also disclosed are methods for the use of lipid-specific antibody compositions, including those specific for PS, in a variety of diagnostic and therapeutic regimens, including the treatment of cancer.

Exemplary preferred methods and compositions according to this invention, which will be described in greater detail in the remainder of the invention include:

Methods for inhibiting cancer cell growth or killing cancer cells, comprising eliciting an immune response with an immunologically effective amount of a composition comprising a phosphatidylserine/polypeptide conjugate;

Methods for treating cancer comprising eliciting an immune response with an immunologically effective amount of a composition comprising a phosphatidylserine/polypeptide conjugate;

Methods for treating cancer comprising contacting a subject with a lipid or lipid/polypeptide conjugate effective to treat said cancer;

Methods of generating an immune response, comprising administering to an animal a pharmaceutical composition comprising an immunologically effective amount of a phosphatidylcholine/polypeptide or a phosphatidylserine/polypeptide conjugate composition;

Methods for treating cancer in an animal, comprising generating in said animal an immune response to a composition comprising a phosphatidyiserine or phosphatidylserine/polypeptide conjugate effective to treat said cancer, Methods of making an antibody that specifically binds to phosphatidylserine or a phosphatidylcholine/polypeptide or a phosphatidylserine/polypeptide conjugate, said methods comprising administering to an animal a pharmaceutical composition comprising an immunologically effective amount of a phosphatidylcholine/polypeptide or a phosphatidylserine/polypeptide conjugate composition. Presently preferred conjugates for use in such methods are, for example, phosphatidylserine/BSA, phosphatidyiserine/KLR phosphatidylserine/BGG, and phosphatidylserine/$\beta_2$-glycoprotein I conjugate;

Antibodies that specifically bind to phosphatidylserine or a phosphatidylcholine/polypeptide or a phosphatidylserine/polypeptide conjugate, said antibody made by a process comprising administering to an animal a pharmaceutical composition comprising an immunologically effective amount of a phosphatidylcholine/polypeptide or a phosphatidyiserine/polypeptide conjugate composition. Presently preferred conjugates for use in such processes are, for example, phosphatidylserine/BSA, phosphatidylserine/KLH, phosphatidylserine/BGG, and phosphatidylserine/$\beta_2$-glycoprotein I conjugate;

Methods for detecting a phosphatidylserine, phosphatidylcholine/polypeptide or a phosphatidylserine/polypeptide conjugate in a biological sample, comprising the steps of:
(a) obtaining a biological sample suspected of containing a phosphatidylcholine/polypeptide or a phosphatidylserine/polypeptide conjugate;
(b) contacting said sample with a first antibody that binds to a phosphatidylcholine/polypeptide or a phosphatidylserine/polypeptide conjugate, under conditions effective to allow the formation of immune complexes; and
(c) detecting the immune complexes so formed; and Immunodetection kits comprising, in suitable container means, an antibody that specifically binds to phosphatidylserine or to a phosphatidylserine/polypeptide conjugate, and an immunodetection reagent.

In an important embodiment, the invention provides antigenic PS conjugate compositions and means for making and using these compositions. In the context of this invention, a PS composition is understood to comprise one or more phosphatidylserine compositions that are able to generate an immune response in an animal. A PS antibody composition is understood to mean an antibody which is specific for PS. Preferably, the antigen composition comprises a lipid-carrier protein conjugate. The carrier protein may be maleimide-activated, or alternatively, may be prepared by introduction of reactive sulfhydryls into the carrier protein. Alternatively, one may prepare proteins by non-covalent electrostatic interactions between negatively-charged anionic phospholipids and lipid binding proteins such as $\beta_2$-glycoprotein I, also known as apolipoprotein H. Exemplary carrier proteins contemplated to be useful in the present methods include various commonly used carrier proteins including BSA (bovine serum albumin), KLH (keyhole limpet hemocyanin), BGG (bovine gamma globulin) and diphtheria toxin. As such, a PS composition of the present invention is also understood to comprise one or more PS-containing or other negatively charged formulations that elicit an immune response in an animal.

2.1 Lipid-specific Antibody Compositions

In a preferred embodiment, administration of a therapeutically effective dose of a lipid-conjugate antigen composition, such as a PS-conjugate to an animal induces in the animal antibodies which are specific for the particular lipid. In one embodiment, the carrier protein is a glycoprotein, such as $\beta_2$-glycoprotein I.

In certain aspects, the present invention concerns novel lipid-carrier antigen compositions which evoke a specific immune response to the lipid. In particular, PS antigen compositions have been developed which have shown remarkable utility both in vitro and in vivo. In particular, PS antigen compositions have been produced to provide vaccine or therapeutic compositions useful in the prevention or treatment of various cancers, such as lymphomas and renal and bladder cancers.

2.2 Methods for Generating an Immune Response

A further aspect of the invention is the preparation of immunological compositions comprising both antibody and cell-mediated immune responses for diagnostic and therapeutic methods relating to the detection and treatment of a variety of cancers and related illnesses.

The invention also encompasses PS antigen and antibody compositions together with pharmaceutically-acceptable excipients, carriers, diluents, adjuvants, and other components, such as peptides, antigens, or pharmaceuticals, as may be employed in the formulation of particular vaccines or antibody compositions.

Antibodies may be of several types including those raised in heterologous donor animals or human volunteers immunized with PS compositions, monoclonal antibodies (mAbs) resulting from hybridomas derived from fuisions of B cells from PS-immunized animals or humans with compatible myeloma cell lines, so-called "humanized" mAbs resulting from expression of gene fusions of combinatorial determining regions of mAb-encoding genes from heterologous species with genes encoding human antibodies, or PS-reactive antibody-containing fractions of plasma from human or animal donors.

Also disclosed is a method of generating an immune response in an animal. The method generally involves administering to an animal a pharmaceutical composition comprising an immunologically effective amount of a PS composition disclosed herein Preferred animals include mammals, and particularly humans. Other preferred animals include murines, bovines, equines, ovines, caprines, opines, porcines, canines, felines, and the like. The composition may include partially or significantly purified PS antigen compositions, and particularly will include one or more of the PS conjugate compositions described herein.

By "immunologically effective amount" is meant an amount of a peptide/lipid composition that is capable of generating an immune response in the recipient animal. This includes both the generation of an antibody response (B cell response), and/or the stimulation of a cytotoxic immune response (T cell response). The generation of such an immune response will have utility in both the production of useful bioreagents, e.g., CTLs and, more particularly, reactive antibodies, for use in diagnostic embodiments, and will also have utility in various prophylactic and therapeutic embodiments.

Immunoformulations of this invention, whether intended for vaccination, treatment, or for the generation of antibodies useful in the detection of PS or other lipids may comprise native, or synthetically-derived PS antigenic compositions produced using the methods described herein. As such, antigenic functional equivalents of the PS compositions described herein also fall within the scope of the present invention. An "antigenically functional equivalent" protein or peptide is one that incorporates an epitope that is immunologically cross-reactive with one or more epitopes derived from any of the particular PS compositions disclosed herein. Antigenically functional equivalents, or epitopic sequences and lipid formulations, may be first designed or predicted and then tested, or may simply be directly tested for cross-reactivity. Also encompassed by the invention are modified PS-conjugates which have improved antigenicity or other desirable characteristics, and that are produced in a fashion similar to those described herein.

In still further embodiments, the present invention concerns immunodetection methods and associated kits. It is contemplated that the PS antigen compositions, and particularly PS conjugates, may be employed to detect antibodies having reactivity therewith, or, alternatively, antibodies prepared in accordance with the present invention, may be employed to detect PS-containing cells, compositions, tissues, and the like. Either type of kit may be used in the immunodetection of compounds, present within clinical samples. The kits may also be used in antigen or antibody purification, as appropriate.

In general, the preferred immunodetection methods will include first obtaining a sample suspected of containing a lipid-specific antibody, such as a biological sample from a patient, and contacting the sample with a first lipid and/or lipid conjugate antigen composition under conditions effective to allow the formation of an immunocomplex (primary immune complex). One then detects the presence of any primary immnunocomplexes that are formed.

Contacting the chosen sample with the lipid antigen composition under conditions effective to allow the formation of (primary) immune complexes is generally a matter of simply adding the antigen composition to the sample. One then incubates the mixture for a period of time sufficient to allow the added antigens to form immune complexes with, i.e., to bind to, any antibodies present within the sample. After this time, the sample composition, such as a tissue section, ELISA plate, dot blot or western blot, will generally be washed to remove any non-specifically bound antigen species, allowing only those specifically bound species within the immune complexes to be detected.

The detection of immunocomplex formation is well known in the art and may be achieved through the application of numerous approaches known to the skilled artisan and described in various publications, such as, e.g., Nakamura et al. (1987), incorporated herein by reference. Detection of primary immune complexes is generally based upon the detection of a label or marker, such as a radioactive, fluorescent, biological or enzymatic label, with enzyme tags such as alkaline phosphatase, urease, horseradish peroxidase and glucose oxidase being suitable. The particular antigen employed may itself be linked to a detectable label, wherein one would then simply detect this label, thereby allowing the amount of bound antigen present in the composition to be determined.

Alternatively, the primary immune complexes may be detected by means of a second binding ligand that is linked to a detectable label and that has binding affinity for the first protein or peptide. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies and the remaining bound label is then detected.

For diagnostic purposes, it is proposed that virtually any sample suspected of containing the antibodies of interest may be employed. Exemplary samples include clinical samples obtained from a patient such as blood or serum samples, cerebrospinal, synovial, or bronchoalveolar fluid, ear swabs, sputum samples, middle ear fluid or even perhaps urine samples may be employed. Such methods may be useful for the diagnosis and treatment of various cellular disorders, and in particular, cancers and related conditions.

Furthermore, it is contemplated that such embodiments may have application to nonclinical samples, such as in the titering of antibody samples, in the selection of hybridomas, and the like. Alternatively, the clinical samples may be from veterinary sources and may include such domestic animals as cattle, sheep, and goats. Samples from murine, ovine, opine, caprine, feline, canine, and equine sources may also be used in accordance with the methods described herein.

In related embodiments, the present invention contemplates the preparation of kits that may be employed to detect the presence of PS-specific antibodies in a sample. Generally speaking, kits in accordance with the present invention will include a suitable lipid, lipid/protein or peptide together with an immunodetection reagent, and a means for containing the lipid, protein or peptide and reagent.

The immunodetection reagent will typically comprise a label associated with a PS antigen composition, or associated with a secondary binding ligand. Exemplary ligands might include a secondary antibody or lipid binding protein directed against the first PS antigen or antibody composition, or a biotin or avidin (or streptavidin) ligand having an associated label. Detectable labels linked to antibodies that have binding affinity for a human antibody are also contemplated, e.g., for protocols where the first reagent is a PS antigen composition that is used to bind to a reactive antibody from a human sample. Of course, as noted above, a number of exemplary labels are known in the art and all such labels may be employed in connection with the present invention. The kits may contain antigen, lipid binding protein, or antibody-label conjugates either in fully conjugated form, in the form of intermediates, or as separate moieties to be conjugated by the user of the kit.

The container means will generally include at least one vial, test tube, flask, bottle, syringe or other container means, into which the antigen may be placed, and preferably suitably allocated. Where a second binding ligand is provided, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

2.3 Immunodetection Kits and Methods

Another aspect of the invention are immunodetection kits containing lipid or lipid-carrier conjugate antigen-specific antibodies and suitable immunodetection reagents such as a detectable label linked to a protein, peptide or the antibody itself. Alternatively, the detectable label may be linked to a second antibody which binds to a lipid-specific antibody as disclosed herein.

Related embodiments include diagnostic and therapeutic kits which include pharmaceutically-acceptable formulations of either the antibodies, lipid, lipid/peptide, or peptide antigens disclosed herein. Such kits are useful in the detection of lipids such as PS in clinical samples, and also useful for promoting an immune response in an animal, and in the formulation of vaccine compositions effective in the treatment of a variety of cancers.

2.4 Vaccine Formulation and Compositions

In certain embodiments, the inventor contemplates the use of the lipid-carrier conjugate compositions for the preparation of anti-cancer vaccines or treatment regimens for administration to an animal, and in particular, a human. It is expected that to achieve an "immunologically effective formulation" it may be desirable to administer a lipid-carrier conjugate composition, such as a PS-carrier antigen composition, to the human or animal subject in a pharmaceutically acceptable composition comprising an immunologically effective amount of an antigen composition mixed with other excipients, carriers, or diluents which may improve or otherwise alter stimulation of B cell and/or T cell responses, or immunologically inert salts, organic acids and bases, carbohydrates, and the like, which promote stability of such mixtures. Immunostimulatory excipients, often referred to as adjuvants, may include salts of aluminum (often referred to as Alums), simple or complex fatty acids and sterol compounds, physiologically acceptable oils, polymeric carbohydrates, chemically or genetically modified protein toxins, and various particulate or emulsified combinations thereof. Lipid conjugate antigen compositions within these mixtures, or each variant if more than one are present, would be expected to comprise about 0.0001 to 1.0 milligrams, or more preferably about 0.001 to 0.1 milligrams, or even more preferably less than 0.1 milligrams per dose.

2.5 Therapeutic and Diagnostic Kits Comprising Lipid-conjugate Antigens or Lipid-specific Antibody Compositions A therapeutic kit comprising, in suitable container means, one or more lipid-conjugate antigen(s) or antibody composition(s) of the present invention in a pharmaceutically acceptable formulation, represents another important aspect of the invention.

The kit may comprise a single container means that contains the lipid-conjugate antigen(s) or antibody composition(s). The container means may, if desired, contain a pharmaceutically acceptable sterile excipient, having associated with it, the lipid-conjugate antigen(s) or antibody composition(s) and, optionally, a detectable label or imaging agent. The formulation may be in the form of a gelatinous composition (e.g., a collagenous composition), a powder, solution, matrix, lyophilized reagent, or any other such suitable means. In certain cases, the container means may itself be a syringe, pipette, or other such like apparatus, from which the lipid-conjugate antigen(s) or antibody composition(s) may be applied to a tissue site, tumor, skin lesion, wound area, or other site of administration. However, the single container means may contain a dry, or lyophilized, mixture of one or more lipid-conjugate antigen(s) or antibody composition(s), which may or may not require pre-wetting before use.

Alternatively, the kits of the invention may comprise distinct container means for each component. In such cases, one or more containers would contain each of the PS composition(s), either as sterile solutions, powders, lyophilized forms, etc., and the other container(s) would include a matrix, solution, or other suitable delivery device for applying the composition to the body, bloodstream, or to a tissue site, skin lesion, tumor cell, wound area, or other site of administration. Such delivery device may or may not itself contain a sterile solution, diluent, gelatinous matrix, carrier or other pharmaceutically-acceptable components.

The kits may also comprise a second or third container means for containing a sterile, pharmaceutically acceptable buffer, diluent or solvent. Such a solution may be required to formulate the lipid-conjugate antigen(s) or antibody composition(s) into a more suitable form for application to the body, e.g., as a topical preparation, or alternatively, in oral, parenteral, or intravenous forms. It should be noted, however, that all components of a kit could be supplied in a dry form (lyophilized), which would allow for "wetting" upon contact with body fluids. Thus, the presence of any type of pharmaceutically acceptable buffer or solvent is not a requirement for the kits of the invention. The kits may also comprise a second or third container means for containing a pharmaceutically acceptable detectable imaging agent or composition.

The container means will generally be a container such as a vial, test tube, flask, bottle, syringe or other container means, into which the components of the kit may placed. The components may also be aliquoted into smaller containers, should this be desired. The kits of the present invention may also include a means for containing the individual containers in close confinement for commercial sale, such as, e.g., injection or blow-molded plastic containers into which the desired vials or syringes are retained.

Irrespective of the number of containers, the kits of the invention may also comprise, or be packaged with, an instrument for assisting with the placement of the lipid-carrier conjugate, or antibodies reactive therewith, within the body of an animal. Such an instrument may be a syringe, needle, surgical instrument, pipette, forceps, or any such medically approved delivery vehicle.

2.6 Antibody Composition and Formulations Thereof

As described above, an important embodiment of the invention is the formulation of lipid-specific antibodies which are useful in detecting and treating various cancers in an animal, and particularly, in a human. Means for preparing and characterizing antibodies are well known in the art (See, e.g., Harlow and Lane (1988); incorporated herein by reference). The methods for generating mAbs generally begin along the same lines as those for preparing polyclonal antibodies. Briefly, a polyclonal antibody is prepared by immunizing an animal with one or more of the lipid-carrier protein compositions disclosed herein and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. With respect to preparing lipid-specific antibodies, it is necessary to boost the host immune system, and may be achieved by coupling the lipid of interest, such as PS, to a carrier. As described above, exemplary and preferred carriers include polypeptide carriers such as KLH, BSA, and $\beta_2$-glycoprotein I. Other albumins such as ovalbumin, mouse serum albumin or rabbit serum albumin can also be used as carriers, as well as bovine gamma globulin and/or diphtheria toxoid. Although means for conjugating lipids to a carrier protein are well-known in the art, two particular synthesis methods are disclosed herein which have been particularly useful in preparing covalent lipid-specific antibody formulations.

mAbs may be readily prepared through use of well-known techniques, such as those exemplified in U.S. Pat. No. 4,196,265, incorporated herein by reference. Typically, this technique involves immunizing a suitable animal with a selected immunogen composition. The immunizing composition is administered in a manner effective to stimulate antibody producing cells. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately about $5 \times 10^7$ to about $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fuision efficiency, and enzyme deficiencies that render them incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Mistein, 1975; 1976), and those using polyethylene glycol (PEG), such as 37% (vol./vol.) PEG, by Gefter et al. (1977). The use of electrically induced fusion methods is also appropriate (Goding, 1986).

Fusion procedures usually produce viable hybrids at low frequencies, about $1 \times 10^{-6}$ to about $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimnmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fuision. The injected animal develops tumors secreting the specific mAb produced by the fused cell hybrid. The body fluids of the animal, such as serum or ascites fluid, can then be tapped to provide mabs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

3.0 BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1. Synthesis method B for producing PS-carrier antigenic conjugates. SPDP-PS is "deblocked" with (tris[2-carboxyethyl]phosphine HCl) to yield a free sulfhydryl which is then directly coupled to maleimide activated carrier proteins.

Figure 2:
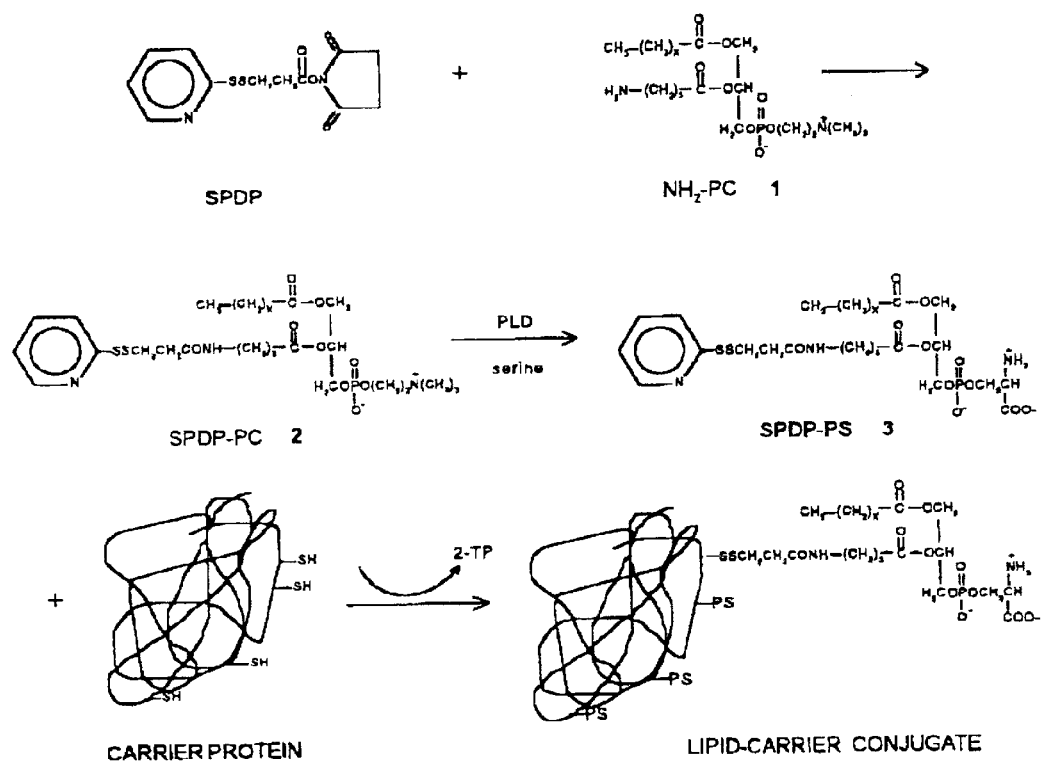

FIG. 2. Synthesis method A for producing of PS-carrier conjugate antigenic conjugates. $NH_2$-PC was acylated with SPDP, converted to the PS derivative with phospholipase D and coupled by thiol-disulphide exchange to carrier protein.

Figures 3A, 3B, 3C:
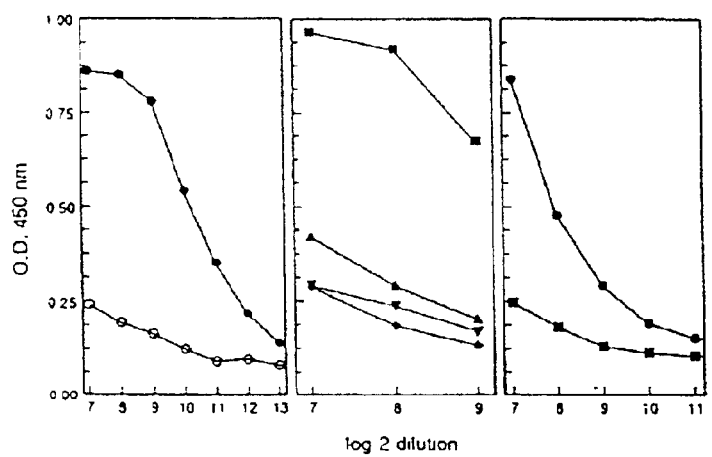

FIG. 3A. Reactivity of rabbit PS antiserum with phospholipids. Microtiter plates were coated with 6 μg of lipid. Bound IgG was quantified by ELISA with peroxidase conjugated goat anti-rabbit Ig. Binding of control pre-immune (○) and antiserum (●) to PS coated plates.

FIG. 3B. Reactivity of rabbit PS antiserum with phospholipids. Microtiter plates were coated with 6 μg of lipid. Bound IgG was quantified by ELISA with peroxidase conjugated goat anti-rabbit Ig. Binding of PS antiserum to polystyrene plates coated with 6 μg of DOPE (■), PA (▲), PG (▼) and PC (♦).

FIG. 3C. Reactivity of rabbit PS antiserum with phospholipids. Microtiter plates were coated with 6 μg of lipid. Bound IgG was quantified by ELISA with peroxidase conjugated goat anti-rabbit Ig. Binding of PS antiserum to polystyrene plates coated with PS/PC(1/1) (●), DOPE/PC (1/1) (■).

Figures 4A, 4B, 4C:
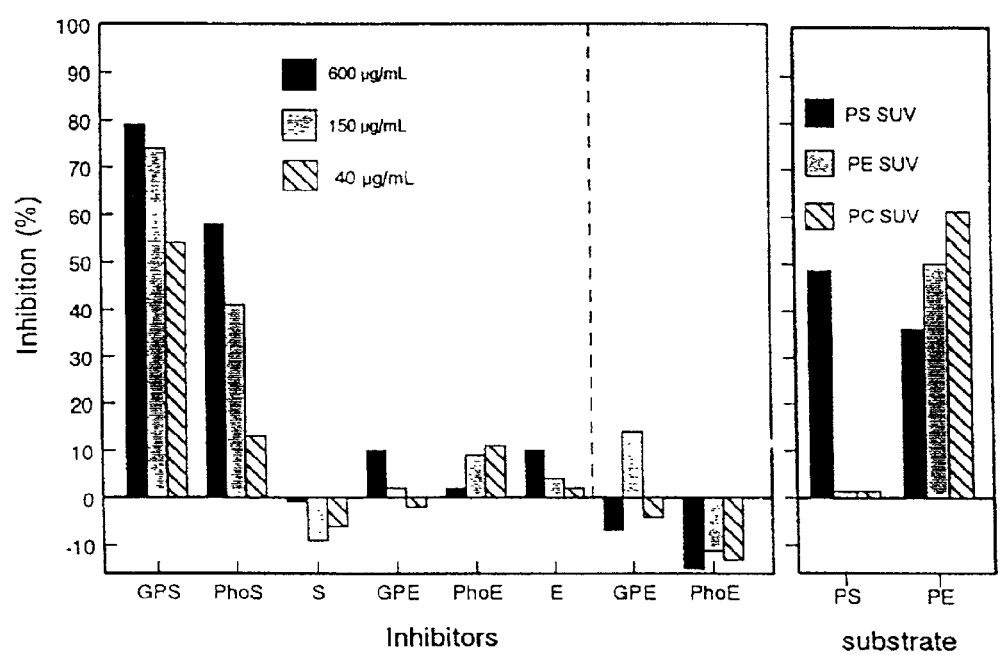

FIG. 4A. Inhibition of immune serum binding with soluble head group analogs and vesicles. The binding assays shown in FIG. 3 were carried out on PS-coated plates in the presence of glycerophosphoserine (GPS), phosphoserine (PhoS), serine (S), glycerophosphoethanolarnine (GPE), phosphoethanolamine (PhoE), and ethanolamnine (E) at the indicated concentrations.

FIG. 4B. Inhibition of immune serum binding with soluble head group analogs and vesicles. The binding assays shown in FIG. 3 were carried out on DOPE-coated plates in the presence of GPE and PhoE at the indicated concentrations.

FIG. 4C. Inhibition of immune serum binding with soluble head group analogs and vesicles. Plates coated with PS and DOPE were assessed for antibody binding in the presence of sonicated vesicles (0.5 mg/ml) containing PS (PS/PC,1/1), DOPE (PE/PC,1/1) and PC.

Figure 5:
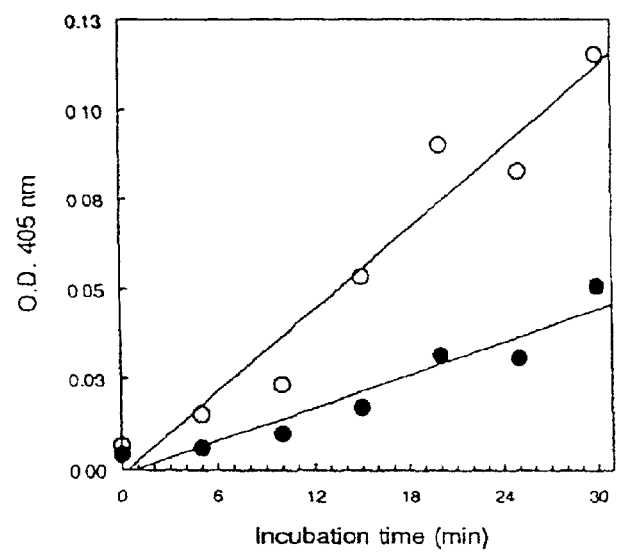

FIG. 5. Inhibition of prothrombinase activity. Prothrombinase activity was assessed in the presence of PS-containing vesicles preincubated with the indicated sera. The reaction was stopped at various time points with EDTA and thrombin production was assessed by determining the initial rates of thrombin-dependent cleavage of the chromogenic substrate. These rates were plotted on the ordinate against the incubation time. Pre-immune serum (○), antiserum (●).

FIG. 6A. Fluorescence microscopy and analysis by flow cytometry of anti-PS treated red blood cells (RBC). Papain-treated RBC were incubated for 1 h with A23187 (5 μM) and $Ca^{2+}$ (1 mM) followed by labeling with the antiserum and fluorescein-conjugated anti-rabbit IgG. Phase photomicrographs of antibody-labeled PS-expressing RBC.

FIG. 6B. Fluorescence microscopy and analysis by flow cytometry of anti-PS treated red blood cells. Papain-treated RBC were incubated for 1 h with A23187 (5 μM and $Ca^{2+}$ (1 mM) followed by labeling with the antiserum and fluorescein-conjugated anti-rabbit IgG. Fluorescence photomicrographs of antibody-labeled PSxpressing RBC.

FIG. 6C. Fluorescence microscopy and analysis by flow cytometry of anti-PS treated RBC. Papain-treated RBC were incubated for 1 h with A23187 (5 μM) and $Ca^{2+}$ (1 mM) followed by labeling with the control serum and fluorescein-conjugated anti-rabbit IgG. Flow cytometry analysis of PS-expressing RBC incubated with control sera.

FIG. 6D. Fluorescence microscopy and analysis by flow cytometry of anti-PS treated RBC. Papain-treated RBC were incubated for 1 h with A23187 (5 μM) and $Ca^{2+}$ (1 mM) followed by labeling with the antiserum and fluorescein-conjugated anti-rabbit IgG. Flow cytometry analysis of PS-expressing RBC incubated with immune sera.

Figure 7:
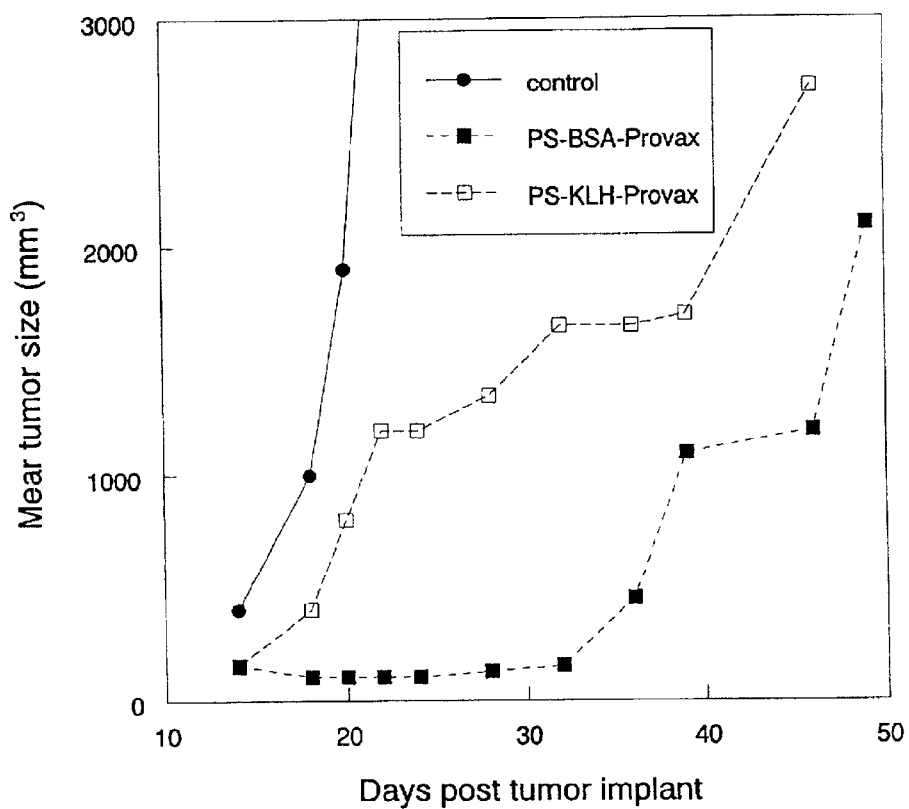

FIG. 7. C57B1/6 mice were inoculated subcutaneously (s.c.) with PS-expressing (determined by the ability of the cells to be stained with the PS-specific reagent, fluorescein-conjugated annexin V) EG7 lymphoma cells. The mice were sorted into treatment groups (6–8 animals/group) when tumors ranged in size between approximately 75–100 $mm^3$ at which time immunization was initiated. The tumor-bearing mice were immunized with a single injection of Provax on day 8 with 100 μg of PS-KLH or PS-BSA conjugate. Tumor growth delays ranged from 38 days for the PS-BSA group and 20 days for the PS-KLH group.

4.0 DESCRIPTION OF ILLUSTRATIVE EMBODIMENTS

4.1 Affinity Chromatography

Affinity chromatography is generally based on the recognition of a protein by a substance such as a ligand or an antibody. The column material may be synthesized by covalently coupling a binding molecule, such as an activated dye, for example to an insoluble matrix. The column material is then allowed to adsorb the desired substance from solution. Next, the conditions are changed to those under which binding does not occur and the substrate is eluted. The requirements for successful affinity chromatography are:

1) that the matrix must specifically-adsorb the molecules of interest;
2) that other contaminants remain unadsorbed;
3) that the ligand must be coupled without altering its binding activity;
4) that the ligand must bind sufficiently tight to the matrix; and
5) that it must be possible to elute the molecules of interest without destroying them.

A preferred embodiment of the present invention is an affinity chromatography method for purification of antibodies from solution wherein the matrix contains a lipid such as PS, or a lipid-conjugate antigen composition, such as a PS-protein conjugate, covalently-coupled to a matrix such as Sepharose CL6B or CL4B. Such a matrix binds the PS-specific antibodies of the present invention directly and allows their separation by elution with an appropriate gradient such as salt, GuHCl, pH, or urea. Another preferred embodiment of the present invention is an affinity chromatography method for the purification of lipid-conjugate antigen compositions from solution In such methods, the matrix would comprise antibodies which specifically bind to the lipid-onjugate antigen compositions of the present invention directly, thus permitting their separation by elution with a suitable buffer as described above.

4.2 Liposomes and Nanocapsules

In certain embodiments, the inventor contemplates the use of liposomes and/or nanocapsules for the introduction of particular antigens or antibodies into host cells. Such formulations may be preferred for the introduction of pharmaceutically-acceptable formulations of the lipid-carrier polypeptide conjugates and/or antibodies disclosed herein. The formation and use of liposomes is generally known to those of skill in the art (see for example, Couvreur et al., 1977 which describes the use of liposomes and nanocapsules in the targeted antibiotic therapy of intracellular bacterial infections and diseases). More recently, liposomes were developed with improved serum stability and circulation half-times (Gabizon and Papahadjopoulos, 1988; Allen and Choun, 1987).

In a further embodiment of the invention, the PS/potypeptide composition may be entrapped in a fiposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

Nanocapsules can generally entrap compounds in a stable and reproducible way (Henry-Michelland et al., 1987). To avoid side effects due to intracellular polymeric overloading, such ultrafine particles (sized around 0.1 $\mu$m) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1977; 1988).

4.3 Methods for Preparing Lipid-specific Antibodies

In another aspect, the present invention contemplates an antibody that is immunoreactive with a lipid such as PS. As stated above, one of the uses for lipid-carrier conjugate antigen compositions according to the present invention is to generate antibodies. Reference to antibodies throughout the specification includes whole polyclonal and monoclonal antibodies (mAbs), and parts thereof, either alone or conjugated with other moieties. Antibody parts include Fab and F(ab)$_2$ fragments and single chain antibodies. The antibodies may be made in vivo in suitable laboratory animals or in vitro using recombinant DNA techniques. In a preferred embodiment, an antibody is a polyclonal antibody. .Briefly, a polyclonal antibody is prepared by immunizing an aimgal with an immunogen comprising a lipid/polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for lipids such as PS may be prepared using conventional immunization techniques, as will be generally known to those of skill in the art. A composition containing lipid antigen compositions described herein may be used to immunize one or more experimental animals, such as a rabbit or mouse, which will then proceed to produce specific antibodies against lipids such as PS. Polyclonal antisera may be obtained, after allowing time for antibody generation, simply by bleeding the animal and preparing serum samples from the whole blood.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate mAbs (below).

One of the important features provided by the present invention is a polyclonal sera that is relatively homogenous with respect to the specificity of the antibodies therein. Typically, polyclonal antisera is derived from a variety of different "clones," i.e., B-cells of different lineage. mAbs, by contrast, are defined as coming from antibody-producing cells with a common B-cell ancestor, hence their "mono" clonality.

To obtain mAbs, one would also initially immunize an experimental animal, often preferably a mouse, with a lipid-carrier protein conjugate-containing composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired peptide.

Following immunization, spleen cells are removed and fused, using a standard fuision protocol with plasmacytoma cells to produce hybridomas secreting mAbs against the antigen compositions. Hybridomas which produce mAbs to the selected antigens are identified using standard techniques, such as ELISA and Western blot methods. Hybridoma clones can then be cultured in liquid media and the culture supernatants purified to provide the lipid-specific mAbs.

It is proposed that the mAbs of the present invention will also find useful application in immunochemical procedures, such as ELISA and Western blot methods, as well as other procedures such as immunoprecipitation, immnunocytological methods, etc. which may utilize antibodies specific to lipids such as PS. In particular, lipid-specific antibodies may be used in immunoabsorbent or affinity protocols as described above to purify lipid-containing compositions. The operation of all such immunological techniques will be known to those of skill in the art in light of the present disclosure.

4.4 Immunoassays

As noted, it is proposed that the lipid-carrier conjugate compositions of the invention will find utility as immunogens, e.g., in connection with vaccine development, or as antigens in immunoassays for the detection of reactive antibodies. Turning first to immunoassays, in their most simple and direct sense, preferred immunoassays of the invention include the various types of enzyme linked immunosorbent assays (ELISAs), as are known to those of skill in the art. However, it will be readily appreciated that the utility of lipid-carrier conjugate compositions is not limited to such assays, and that other useful embodiments include RIAs and other non-enzyme linked antibody binding assays aid procedures.

In preferred ELISA assays, proteins or peptides incorporating lipid-carrier conjugate compositions are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the test antisera, such as bovine serum albumin (BSA) or casein, onto the well. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for, e.g., from 2 to 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound lipid-carrier conjugate composition, and subsequent washing, the occurrence and the amount of immunocomplex formation may be determined by subjecting the complex to a second antibody having specificity for the first. Of course, in that the test sample will typically be of human origin, the second antibody will preferably be an antibody having specificity for human antibodies. To provide a detecting means, the second antibody will preferably have an associated detectable label, such as an enzyme label, that will generate a signal, such as color development upon incubating with an appropriate chromogenic substrate. Thus, for example, one will desire to contact and incubate the antisera-bound surface with a urease or peroxidase-conjugated anti-human IgG for a period of time and under conditions that favor the development of immunocomplex formation (e.g., incubation for 2 hours at room temperature in a PBS-containing solution such as PBS-Tween®)).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)sulfonic acid (ABTS) and $H_2O_2$, in the case of peroxidase as the enzyme label. Quantitation is then achieved by measuring the degree of color generation, e.g., using a visible spectrum spectrophotometer.

ELISAs may be used in conjunction with the invention. In one such ELISA assay, proteins or peptides incorporating antigenic sequences or moieties of the present invention are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of powdered milk. This allows for blocking of nonspecific adsorption sites on the immobilizing surface and thus reduces the background caused by nonspecific binding of antisera onto the surface.

4.5 Immunoprecipitation

The lipid-carrier conjugate-specific antibodies of the present invention are particularly useful for the isolation of lipid-containing compositions by immunoprecipitation. Immunoprecipitation involves the separation of the target antigen component from a complex mixture, and is used to discriminate or isolate minute amounts of protein. For the isolation of cell-surface localized compositions, such as PS, these compositions may be solubilized from the cell by treatment with enzymes, or alternatively, into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g., enzyme-substrate pairs.

4.6 Western Blots

The lipid antigen and lipid-specific antibody compositions of the present invention find great use in a variety of immunoblot and western blot analyses. For example, the PS-specific antibodies may be used as high-affinity primary reagents for the identification of PS-containing compositions immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods in conjunction with Western blotting (including enzymatically-, radiolabel-, or fluorescently-tagged secondary antibodies against the toxin moiety) are considered to be of particular use in this regard.

4.7 PS Compositions for Treating Cancer

The maintenance of a particular lipid bilayer equilibrium distribution, in particular the preservation of PS in the cell's inner leaflet, is a property characteristic of normal, mature cells. If the translocation machinery becomes impaired, such as in tumor cells, PS appears at the cell surface and invokes substantial functional consequences.

The inventor contemplates that the PS compositions described herein may be used for the prevention of or the treatment of essentially any disorder that is characterized by the presence of PS on the surface of the cell. Cancers having such a characteristic may include those of the brain, lung, liver, spleen, kidney, bladder, lymph node, small intestine, pancreas, blood cells, colon, stomach, breast, endometrium, prostate, testicle, ovary, skin, head and neck, esophagus, or bone marrow. In preferred embodiments, the cancerous cells are derived from the kidney, bladder, lymph nodes or bone marrow.

4.8 Pharmaceatical Compositions

In certain embodiments, the pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Alternatively, in some embodiments, it may be desirable to administer the antigen or antibody compositions disclosed either intravenously, parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it win be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuumdrying and freeze-drying techniques which yield a powder of the active ingredient plus any additional desired ingredient from a previously sterile-filtered solution thereof As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

4.9 Vaccine Preparation

The compositions described herein provide immunogenic particles that are able to elicit an anti-PS immune response. Because PS generally is found on the surface of aberrant cell types (e.g., tumor cells and apoptotic cells), the inventor contemplates that such compositions are ideal for use as a potential vaccine against tumorigenesis. Thus the present invention provides an immunogenic composition that may be used as a vaccine against cancer.

In certain embodiments, such vaccines may be injectable liquid solutions or emulsions. The PS compositions disclosed herein may be mixed with pharmaceutically-acceptable excipients which are compatible with the PS compositions. By compatible it is meant that the phamaceutically-acceptable excipients will not alter the conformational characteristics of the immunogen. Excipients may include water, saline, dextrose, glycerol, ethanol, or combinations thereof. The vaccine may further contain auxiliary substances, such as wetting or emulsifying agents, buffering agents, or adjuvants to enhance the effectiveness of the vaccines. Adjuvants may be mineral salts (e.g., AlK$(SO_4)_2$, AlNa$(SO_4)_2$, AlNH$_4$$(SO_4)$, silica, alum, Al$(OH)_3$, Ca$_3$$(PO_4)$, kaolin, or carbon), polynucleotides (e.g., poly IC or poly AU acids), and certain natural substances (e.g., wax D from *Mycobacterium tuberculosis*, substances found in *Corynebacterium parvum*, *Bordetella pertussis*, or members of the genus *Brucella*)(Int. Pat. Appl. Publ. No. WO 91/09603). Aluminum hydroxide or phosphate (alum) are commonly used at 0.05 to 0.1 percent solution in phosphate buffered saline. Other adjuvant compounds include QS2 or incomplete Freunds adjuvant. A preferred adjuvant is Provax (IDEC Pharmaceuticals).

Vaccines may be administered parenterally, by injection subcutaneously or intramuscularly, or the vaccines may be formulated and delivered to evoke an immune response at the mucosal surfaces. The immunogenic composition may be administered to a mucosal surface by the nasal, oral, vaginal, or anal routes. For anal delivery, suppositories may be used. Suppositories may comprise binders and carriers such as polyalkalene glycols or triglycerides. Oral formulations may be in the form of pills, capsules, suspensions, tablets, or powders and include pharmaceutical grades of saccharine, cellulose or magnesium carbonate. These compositions may contain from about 5% to about 95% of the PS composition or more as needed.

Preferably the vaccines are administered in a manner and amount as to be therapeutically effective. That is to say that the vaccine should be administered in such a way as to elicit an immune response to PS. Suitable doses required to be administered are readily discernible by those of skill in the art. Suitable methodologies for the initial administration and booster doses, if necessary, maybe variable also. The dosage of the vaccine may depend on the route of administration and may vary according to the size of the host.

Although the immunogenic compositions of the present invention may be administered to individuals that have not been diagnosed with cancer, they also may be administered to individuals who have been diagnosed with cancer in an effort to alter the immune response to the tumor. The alteration may be an increase in antibody production, a stimulation of anti-tumor CD4$^+$ or CD8$^+$ T cells, or in respect to the type of response to the virus (i.e., $T_H1$ vs. $T_H2$). Nonetheless, this alteration, if effective, will decrease the mortality and morbidity associated with the cancer. In other words, the immunogenic compound may decrease the severity of the disease and increase the life of the patient.

4.10 Contemporary Cancer Therapy

Most attempts to promote a therapeutic immune response against cancer have been directed towards unique, tumor-specific, peptide or carbohydrate antigens. Little or no attention, however, has been given to the possibility that specific anti-lipid responses might also be exploited for this purpose. Although phospholipids are ubiquitous, it is clear that the organization and membrane sidedness of individual lipid species is not random but is controlled by transport mechanisms that maintain specific transmembrane lipid distributions (Devaux and Zachowski, 1994; Menon, 1995). Recent data suggests that while membrane organization is tightly regulated over the lifespan of the cell, normal lipid distributions are not maintained upon the cell's acquisition of several pathologic phenotypes (Zwaal and Schroit, 1997). This is particularly evident for tumorigenic cells where phosphatidylserine (PS) redistributes from the cell's inner leaflet (its normal location) to the outer leaflet upon transformation (Connor et al., 1989; Utsugi et al., 1991). This condition raises the possibility that PS on the cell's outer leaflet can serve as a target for therapeutic intervention.

4.11 Membrane Lipid Asymmetry and Recognition of PS-expressing Cells

The outer leaflet of eukaryotic cell membranes contains most of the cholinephospholipids, whereas the aminophospholipids are mainly present in the cell's inner leaflet (Verkleij et al., 1973; Zwaal et al., 1975). Although asymmetry seems to be the rule for normal cells, loss of membrane lipid sidedness, in particular the emergence of PS at the cell surface, results in the expression of altered surface properties that modulates cell function and influences the cell's interaction with its environment (Zwaal and Schroit, 1997). For example, the exposure of PS promotes coagulation and thrombosis by platelets (Bevers et al., 1982) and is involved in the recognition and elimination of apoptotic cells (Fadok et al., 1992), senescent cells (Connor et al., 1994) and tumorigenic cells (Utsugi et al., 1991) by phagocytes.

4.12 Autoimmunity and Cancer

Antiphospholipid antibodies (APA) have been demonstrated mainly in sera of patients with connective tissue disease, particularly systemic lupus erythematosus (Mackworth-Young, 1990; Asherson and Cervera, 1993). Although less frequent, APA have also been detected in patients with malignancies, including leukemia, lymphoma, epithelial malignancies and thymoma (Becker and Brocker, 1995; Naldi et al., 1992). Recent studies showed that APA levels were significantly higher in melanoma patients who received immunotherapy with interferon-α or bacillus Calmette-Guerin (Becker et al., 1994; Herstoff and Bogaars, 1979). Furthermore, ongoing preclinical studies investigating the relationship between autoimmunity in leukemia patients treated with interferon-α showed a strong relationship between hematologic/clinical remissions and the levels of APA. Because autoantibodies in patients with autoimmune diseases are capable of binding and killing cells that display the autoantigens, it is possible that the appearance of APA in some cancers, possibly as a consequence of the disease and/or treatment regimen, is responsible for the remissions commonly seen upon interferon-α treatment.

Because PS seems to be a ubiquitous marker for cancer cells, it may serve as a specific epitope for tumor cell populations and a therapeutic target for cancer treatment. To test the feasibility of this approach, an autoimmune APA syndrome-like response against PS was raised in mice using unique immunogens that preserve the lipid's critical head-group and presents PS as a carrier-bound hapten. Studies have shown that mice immunized with these PS-carrier systems using Provax adjuvant (IDEC Pharmaceuticals) are protective against the growth of several syngeneic carcinomas.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Production and Characterization of Polyclonal PS Antibodies

Because PS can be considered to be a non-immunogenic hapten, the inventor reasoned that an appropriate lipid-protein conjugate might elicit a potent and specific immune response. To address this issue and overcome the inherent problems of lipid immunogenicity and cross-reactivity, the inventor synthesized PS that contained a "sulfhydryl-activated" coupling group at the end of the 2-position side chain and covalently linked the lipid to a protein carrier (Diaz et al., 1998). The inventor shows that this antigen induced the production of PS-specific antibodies in primates, rabbits and mice and that these antibodies bound specifically to PS-expressing red blood cells (RBC). The inventor's results suggest that PS antibodies could be an important tool for the study of PS-dependent processes and its distribution in the membranes of living cells.

5.1.1 Materials and Methods

5.1.1.1 Materials

PS, dioleoylphosphatidic acid (PA), PC, dioleoylphosphatidylglycerol (PG), DOPE was purchased from Avanti Biochemicals (Pelham, Ala.). 1-acyl-2-(aminocaproyl) phosphatidylcholine ($NH_2$-PC) was synthesized as previously described (Schroit and Madsen, 1983). N-succinimidyl-3-(2-pyridyldithio) propionate (SPDP) and 2-iminothiolane were purchased from Pierce (Rockford, Ill.). Bovine serum albumin (BSA), keyhole limpet hemocyanin (KLH), prothrombin, factor X and analytical reagents were from Sigma (St. Louis, Mo.). S2238 was purchased from Kabi Laboratories (Franklin, Ohio). Human RBC were obtained from healthy volunteers by venipuncture into heparinized syringes.

5.1.1.2 Synthesis of 1-Acyl-2-N-succinimidyl-3-(2-pyridyldithio) Propionyl(Aminocaproyl)-PS (SPDP-PS)

SPDP-PS was made from SPDP-PC by phospholipase D catalyzed base-exchange in the presence of L-serine (Conifuirius et al., 1990). Briefly, SPDP-PC was synthesized first by reacting 20 μmol of $NH_2$-PC [prepared by deblocking 1-acyl-2-tBOC-aminocaproyl-PC (Schroit and Madsen, 1983)] with 40 μmol of SPDP in 3 ml of $CHCl_3$/MEOH/triethylamine (1/2/0.015) overnight. $CHCl_3$ (1 ml) and water (1.8 ml) was added and the lower organic phase was removed. Analysis of the product, SPDP-PC, by thin-layer chromatography (TLC) ($CHCl_3$/MEOH/$H_2O$; 65/25/4; Rf=–0.4) revealed a single phosphate positive, ninhydrin negative spot. The lipid was then dried and resuspended in 1 ml of 50% L-serine in 0.1M acetate buffer, pH 5.6 containing 0.1M $CaCl_2$. 1 ml of ether and 25 units (70 μl) of phospholipase D was added and the suspension was mixed at 45° C. for 3 h and stopped by the addition of EDTA (to 0.2 M). The ether was then evaporated and the product was resuspended in $CHCl_3$/MEOH/$H_2O$ (1/2/0.8). Excess L-serine was removed by centrifugation. The product was recovered from the organic phase after the addition of 1 part $CHCl_3$ and 1 part water. The organic phase was taken to dryness, dissolved in $CHCl_3$, and applied to a 2×30 cm column of activated prewashed silica gel. The column was washed with 100 ml of $CHCl_3$, followed by 100 ml aliquots of $CHCl_3$ containing increasing MEOH. Analysis of the product which eluted with $CHCL_3$/MEOH (6/4) by TLC revealed a single phosphate and ninhydrin-positive spot (Rf=–0.2). The purified product was stored in $CHCl_3$. Electrospray mass spectra analysis calculated for SPDP-PS [$C_{38}H_{63}N_3O_{11}PS_2$] (M) 833.02, found 832.

5.1.1.3 Coupling of SPDP-PS to Protein Carriers

SPDP-PS was coupled to BSA or KLH after introducing additional sulthydryls into the proteins with 2-iminothiolane. Briefly, the carrier proteins were solubilized at 10 mg/ml in 10 mM Tris buffer pH 8.0 which contained 0.1 mM EDTA. A 100-fold mole excess of 2-iminothiolane was added and the reaction was allowed to proceed for 1 h (Jue et al., 1978). The solution was then dialyzed overnight. To ensure the availability of maximum free sulfhydtyls for coupling, the protein was reduced with 5 mM dithiothreitol (DTT). DTT was removed immediately before coupling by exclusion chromatography on a Biogel P6 column. Peak fractions were collected, and available sulfhydryls were estimated with Eliman's reagent (DTNB) (Riddles et al., 1983). The reduced protein was then immediately mixed with 1 mol equivalent of SPDP-PS in ⅒th volume of ETOH. The efficiency of derivatization was estimated by measuring the release of 2-thiopyridine at 343 nm (Grasseti and Murray, 1967).

5.1.1.4 Immunization Protocol

Rabbits were injected in multiple intradermal sites with ~1 mg of the lipid-protein conjugates in complete Freund's adjuvant followed by a boost one month later in incomplete Freund's adjuvant. The rabbits were bled two weeks after the last injection.

5.1.1.5 Enzyme-linked Immunoabsorbent Assays (ELISA)

Polystyrene microtitre plates were coated overnight at room temperature with 30 µl/well of 200 µg/ml solution of different phospholipids (AVANTI) in $CHCl_3$/MEOH (1/50). Blocking of the dried plates was carried out with 10% goat serum in 0.8% NaCl/20 mM Tris, pH 8.0 for 1 h at room temperature. Antiserum samples prepared in blocking solution were applied to the wells at different dilutions (reported in the figures) for 2 h and binding was assessed by adding anti-rabbit (whole molecule) peroxidase conjugate (SIGMA) at a 1:10,000 dilution in the same buffer for 2 h. TMB-ELISA (3,3'5,5' tetramethylbenzidine base, GIBCO BRL) was used as the substrate. Inhibition of immune serum binding to PS was determined with the head group analogs glycerophosphorylserine (GPS), phosphorylserine (PhoS), serine, glycerophosphorylethanolamine (GPE), phosphorylethanolamine (PhoE), and ethanolamine at 600 µ/ml, 150 µg/ml, and 40 µg/ml. Inhibition with sonicated vesicles (0.5 mg/ml) composed of PS (50 mol % in PC), DOPE (50 mol % in PC), and PC was achieved by the addition of equal volumes of liposomes to antiserum samples diluted in 10% goat serum. After 1 h of incubation at 37° C., ELISA was carried out as described above.

5.1.1.6 Protherombinase Activity Assay

The PS-dependent prothrombinase assay was carried out as described previously (Diaz et al., 1996) except that sonicated PS vesicles (SUV) were used as the procoagulant surface. Briefly, 0.05 ml of PS SUV (1 mg/ml) were incubated with 0.05 ml of antiserum or control preimmune serum for 15 min at 37° C. The suspension was then added to 0.2 ml of prothrombinase assay buffer containing $Ca^{2+}$ and the necessary coagulation factors for the period of time indicated. Aliquots of the suspension were then transferred to a cuvette containing 1 ml of EDTA buffer to stop the production of thrombin. The thrombin-dependent chromogen, S2238, was added to the cuvettes (to 0.2 mmol/l), and the rate of chromophore formation was monitored at 405 nm with a Gilford Response Spectrophotometer employing appropriate kinetic software. The initial rate of thrombin-dependent chromophore production was determined from the slope of the absorbance curve. These rates were plotted on the ordinate against the incubation time.

5.1.1.7 Immunocytochemistry $Ca^{2+}$-induced scrambling of RBC lipids was done by incubating papain-treated RBC (0.25 mg/ml papain, 1 mM EDTA, 2 mM cysteine-HCl in phosphate-buffered saline for 1 h at 37° C.) with 5 µM A23187 in 1 mM $CaCl_2$ for 1 h at 37° C. After removing red cell vesicles by centrifugation, the cells were incubated with anti-PS for 1 h at 0° C. The cells were then washed and stained with fluorescein-conjugated goat anti-rabbit IgG.

5.1.1.8 Flow Cytometry

Data acquisition and analysis were done on a Coulter Epics Profile flow cytometer using EPICS elite software. Forward and side angle light scatter were set to eliminate red cell ghosts. Fluorescence channels were set logarithinetically.

5.1.2 Results

5.1.2.1 Synthesis Method a for Preparation of PS-carrier Conjugates

To preserve the integrity of the lipids reactive serine headgroup, the inventor generated a carboxyl- and amine-independent reactive disulfide group at the acyl side chain, which was done by acylating $NH_2$—PC with SPDP. The product, containing a protected disulfide β chain, was then converted to the PS derivative with phospholipase D (FIG. 2). Lipid/protein coupling was accomplished by disulfide exchange of the lipid haptens to proteins treated with 2-iminothiolane (1 mol SPDP-PS/mol SE). Coupling was stoichiometric as estimated by monitoring the release of 2-thiopyridine. Coupling ratios were typically 20/1 and 135/1 for BSA and KLH, respectively (Table 1).

TABLE 1

COUPLING OF SPDP-PS To AVAILABLE SULFHYDRYL-REACTIVE SITES ON CARRIER PROTEINS

|  | BSA | BSA + Traut's | KLH | KLH + Traut's |
|---|---|---|---|---|
| SH[a] | 3 | 20.6 | 52.9 | 135.8 |
| 1-TP release[b] |  | 100.7% |  | 99.6% |

[a]Reduced sulfhydryls were quantified with DTNB before and after treating the proteins with an excess of 2-iminothiolane/DTT. The reduced protein was then immediately mixed with SPDP-PS (mol/mol).
[b]Coupling efficiency was estimated by comparing free sulfhydryls on the carrier protein to the release of 2-thiopyridine upon the addition of SPDP-PS.

5.1.2.2 Specificity of PS Antibodies

Antisera obtained from rabbits immunized against PS-BSA were tested by ELISA for their ability to bind different phospholipids. The data shown in FIG. 3A, FIG. 3B, and FIG. 3C indicate that the antiserum reacted with PS and DOPE, but not with PC or other negatively charged phospholipids. To determine whether the reaction to DOPE was polar-head group-specific or due to interactions with other structures that might be adopted by DOPE (Rauch et al., 1986; Rauch and Janoff, 1990), binding was tested against lipids deposited as 50 mol % mixtures with PC. FIG. 3C shows that while reactivity to PS was preserved, antibody binding to 50 mol % mixtures of DOPE in PC was similar to the levels obtained with PC alone.

To determine which epitope was responsible for PS binding, the reactivity of the antibodies to the lipid's polar head group was assessed by competitive inhibition with lipid analogs and liposomes of different lipid composition (FIG. 4A, FIG. 4B, and FIG. 4C). At the highest concentration tested, GPS and PhoS, inhibited binding to the PS coated plates by ~80% and 60%, respectively. Serine, GPE, PhoE and ethanolamine were without effect (FIG. 4A). Consistent with the results presented in FIG. 3C, GPE and PhoE did not inhibit antibody binding to DOPE (FIG. 4B), suggesting that antibody reactivity to DOPE was independent of the lipid's polar head group. This was verified by the ability of SUV, irrespective of lipid composition, to inhibit binding to DOPE- but not to PS-coated plates (FIG. 4C).

Because these antibodies bind PS, they should also be able to interfere with PS-dependent processes such as coagulation. To test this, PS vesicles were preincubated with the antiserum for 1 h at 37° C. and the ability of the vesicles to promote the PS-dependent prothrombinase reaction was assessed. The results presented in FIG. 5 show that the initial rates of thrombin-dependent S2238 cleavage after the indicated reaction times were inhibited by ~60% in the antiserum-treated samples (calculated from the slopes of the fitted curve).

5.1.2.3 Generation of PS Antibodies In Primates

Cynomolgus monkeys are immunized with 100 to 250 pg of PS-KLH every two to three weeks. The monkeys were bled every two weeks and the sera was tested in serial dilutions for anti-PS activity in a direct PS-ELISA. One monkey responded with a reciprocal anti-PS titer of ~2700. Anti-PS titers slowly declined over a period of 5 months. The PS-BSA conjugate (250 µg) was then used in subsequent immunizations. Reciprocal anti-PS titers steadily increased in both rabbits after each immunization to ~24, 300.

5.1.2.4 Detection of Cell Surface PS By Immunofluorescence

Red cells were induced to express PS at the cell surface by $Ca^{+2}$ influx which results in interleaflet lipid mixing (Sims et al., 1989; Baldwin et al., 1990; Bevers et al., 1992; Gaffet et al., 1995). The presence of PS on the ionophore treated cells was confirmed by assessing their PS-dependent prothrombinase activity. Cells treated with ionophore and $Ca^{2+}$ were incubated with PS antibodies followed by fluorescein conjugated anti-Rabbit IgG. Fluorescence microscopy showed that these cells were strongly fluorescent (FIG. 6B). Cells treated with preimmune serum were not fluorescent (FIG. 6A) nor were control RBC (cells treated with ionophore alone or $Ca^{+2}$ alone) incubated with preimmune or immune serum. Staining of the $Ca^{+2}$/ionophore-treated RBC was also quantified by flow cytometry. Analysis of RBC incubated with antiserum followed by fluorescein-conjugated anti-rabbit IgG showed that 44% of the population was within the gated area (FIG. 6D) above the background fluorescence of control cefls (FIG. 6C).

5.1.3 Discussion

Various methods have been used to determine the presence of PS on cell membranes. These include direct chemical modification with membrane impermeable reagents such as trinitrobenzenesulfonic acid and hydrolysis with specific phospholipases (Gordesky et al., 1975; Etemadi 1980), direct labeling with PS binding proteins (Thiagarajan and Tait, 1990; Tait and Gibson, 1994; Vermes et al., 1995; Kuypers et al., 1996), and PS-dependent catalysis of coagulation (Rosing et al., 1980; Van Dieijen et al, 1981). Several laboratories used lipid antibodies to detect cell surface PS (Maneta-Peyret et al., 1993; Rote et al., 1993; Rote et al., 1995; Katsuragawa et al, 1995). However, many of these antibodies are not specific and cross-reactivity is common. This may be due to the weak antigenic presentation of the phosphorylated head groups that are critical to specificity or to the generation of antibodies to diacylglycerol, phosphodiester and/or fatty acid moieties that are common to all phospholipids. In an attempt to produce specific PS antibodies, the inventor immunized rabbits with PS covalently coupled to bovine serum albumin or KLH via its fatty acid side chain without modifying the crucial phosphoserine moiety.

These data show that rabbit antibodies recognize PS and 100 mol % DOPE but not PG or PC. The reactivity against pure DOPE, however, seems to be unrelated to the lipids polar head group because reactivity was abolished when the antigen contained 50 mol % PC (FIG. 3C). Moreover, in contrast to the specific inhibition to PS binding obtained with water-soluble PS analogs and PS-containing vesicles, GPE and PhoE did not inhibit antibody binding to DOPE coated plates (FIG. 4B), whereas all vesicles, irrespective of lipid composition, did. Although these results suggest that the antibodies do not specifically bind DOPE, the inventor cannot rule out the possibility that some antibodies recognize hexagonal phase structures adopted by DOPE under certain conditions (Rauch et al., 1986; Rauch and Janoff, 1990). The moiety responsible for the specificity of binding to PS is dependent on the presentation of both the serine head group and the glycerophosphate moiety. Indeed, phosphate groups have been shown to be immunogenic and some phospholipid antibodies are partially inhibited by phosphate buffers and phosphorylated nucleotides (Banedi and Alving, 1990; Alving, 1986). In any event, it is clear that these antibodies are able to recognize PS but not DOPE in a bilayer membrane because of the specific inhibition obtained with PS-containing liposomes in the ELISA (FIG. 4C). Furthermore, fluorescence microscopy and flow cytometry analysis showed that these antibodies did not bind normal RBC even though these cells express ~20% of their total phosphatidylethanolamine at the cell surface. On the other hand, RBC became intensely fluorescent upon expression of PS at the cell surface by $Ca^{2+}$-induced membrane lipid scrambling (Sims et al., 1989; Baldwin et al., 1990; Bevers et al., 1992; Gaffet et al., 1995).

5.2 Example 2

Induction of Autoimmunity for Prevention of Cancer

Cell membranes contain numerous phospholipid species all of which are structurally and organizationally tightly regulated over the lifespan of the cell. A large body of evidence indicates that phosphatidylserine (PS), unlike other phospholipid species, undergoes a dramatic redistribution in the cell's plasma membrane and becomes expressed in the cell's outer membrane leaflet upon acquisition of a pathologic phenotype. Phenotype-dependent redistribution of PS has been shown to occur during programmed death cell (apoptosis), platelet activation, cell aging and tumorigenesis. Because PS seems to be a ubiquitous marker of these pathologic cells, it may serve as a specific target epitope for aberrant cell populations and a therapeutic target for cancer treatment. To test the feasibility of this approach for the treatment of cancer, an autoimmune response against PS was raised in mice using the disclosed immunogens that preserve the lipid's critical head-group and presents PS as a carrier bound hapten.

5.2.1 Synthesis Method B for Prevention of PS-carrier Production

The method is similar to that shown in Example 1 except, instead of coupling PS to a sulfhydryl-bearing carrier protein via thiol-disulphide exchange, SPDP-PS is "deblocked" with (tris[2-carboxyethyl]phosphine HCl) to yield a free sulfhydryl which is then directly coupled to maleimide activated carrier proteins (FIG. 1).

5.2.2 Immunization Against PS Restricts Tumor Growth and Metatasis

To test whether an autoimmune anti-PS response is protective, growth of several transplantable mouse tumors were determined in mice preimmunized with lipid antigen.

5.2.2.1 Mouse MBT-2 Murine Bladder Carcinoma

C3H mice were given subcutaneous immunizations with 0.1 ml of saline (0.9% NaCl) or 0.1 ml of BSA-PS immunogen on day 0 with Provax adjuvant (IDEC Pharmaceuticals) and again on day 7 (1 mg/ml BSA-PS in saline:Provax 2:1). On day 14 the mice were injected with $5 \times 10^4$ syngeneic murine MBT-2 bladder carcinoma cells into the wall of the bladder. On day 38–40, the mice were necropsied and the bladders were removed, weighed, and the presence or absence of tumor was confirmed histologically (Table 2).

TABLE 2

MOUSE MBT-2 MURINE BLADDER CARCINOMA

Individual bladder weights (grams)

| | Control | PS immunized |
|---|---|---|
| | 0.155 | 0.039 |
| | 0.149 | 0.048 |
| | 0.144 | 0.047 |
| | 0.150 | 0.046 |
| | 0.152 | 0.040 |
| | 0.155 | 0.043 |
| | 0.148 | 0.047 |
| | 0.150 | 0.039 |
| | 0.151 | 0.036 |
| mean | 0.150 | 0.049 |
| (range) | (0.144–0.155) | (0.039–0.048) |

Mann-Whitney U-test: Control vs PS immunized, p < 0.0001

5.2.2.2 RENCA Murine Adenocarcinoma

BALB/c mice were given subcutaneous immunizations with 0.1 ml saline or 0.1 ml of KLH-phosphatidylcholine (PC), or 0.1 ml of KLH-PS immunogen on day 0 with Provax adjuvant (IDEC Pharmaceuticals) and again on day 7. Immmunogens were 1 mg/ml in saline:Provax 2:1. On day 14 the mice were given intravenous injections of 1.2× $10^4$ syngeneic RENCA adenocarcinoma cells. On day 38–40, the mice were necropsied for the presence of lung metastasis. Lungs were placed in Bouin's solution and the individual metastasis enumerated (Table 3).

TABLE 3

RENCA MURINE ADENOCARCINOMA

Individual Number of Lung Metastasis

| Control | KLH-PC immunized | KLH-PS immunized |
|---|---|---|
| 10 | 8 | 5 |
| 7 | 8 | 2 |
| 7 | 5 | 1 |
| 5 | 5 | 1 |
| 5 | 4 | 1 |
| 3 | 4 | 0 |
| | 3 | 0 |
| | 1 | 0 |
| Xmed = 6.0 | Xmed = 4.5 | Xmed = 1.0 |

Mann-Whitney U-test:
Control vs KLH-PC, N.S. (p > 0.05)
Control vs KLH-PS, p > 0.02
KLH-PC vs KLH-PS, p > 0.005

5.3 Example 3

Induction of Autoimmunity for Immunotherapy of Cancer

BALB/c mice were given an intravenous injection of 20,000 RENCA cells on day 0 and therapy was started on day 3, comprising no further treatment (controls), or immunization with the 0.1 ml of PS-BSA preparation (1 mg/ml antigen in saline:Provax 2:1). 100 μwas given in two sites the first week, followed by two injections of 50 μg in two sites 7 and 14 days later. The mice were monitored and lungs were harvested on day 31 and the number of individual tumor nodules enumerated (Table 4).

TABLE 4

THERAPY OF EXPERIMENTAL METASTASIS OF MURINE RENAL ADENOCARCINOMA BY AUTOREACTIVE ANTI-LIPID IMMUNITY

Number of Lung Metastasis

| | Control | PS-BSA Immunized |
|---|---|---|
| | 21 | 11 |
| | 14 | 8 |
| | 13 | 5 |
| | 11 | 2 |
| | 9 | 2 |
| median | 13 | 5 | p < 0.05

5.4 Example 4

Induction of Autoimmunity for Immunotherapy of Leukemia

C57B1/6 mice were inoculated subcutaneously (s.c.) with PS-expressing EG7 lymphoma cells (determined by the ability of the cells to be stained with the PS-specific reagent, fluorescein-conjugated annexin V). The mice were sorted into treatment groups (6–8 animal/group) when tumors ranged in size between approximately 75–100 $mm^3$ at which time immunization was initiated. The tumor-bearing mice were immunized with a single injection of Provax on day 8 with 100 μg of PS-KLH or PS-B SA conjugate. Tumor growth delays ranged from 28 days for the PS-BSA group and 20 days for the PS-KLH group (FIG. 7). Given the fast growth rate of this tumor, (tumor volume doubles every 2.4 days) this growth represents a 11.6 (PS-BSA) and 8.5 (PS-KLH) fold decrease in the tumor doubling time.

5.5 Example 5

Induction of Autoimmunity for the Therapy of Cancer Utilizing $\beta_2$-glycoprotein I/Lipid Complexes $\beta_2$-glycoprotein I is a 50 kDa serum glycoprotein (Poltz and Kostner, 1979; Wurm, 1984) that binds to negatively charged phospholipids. While its function is not clear, it has recently been shown that several autoimmune responses (Galli et al., 1990; McNeil et al, 1990; OoSting et al., 1993; Roubey, 1994) are directed against $\beta_2$-glycoprotein I/lipid complexes (Schousboe, 1979). Because many cancer cells express phosphatidylserine on the cell surface, the generation of an anti-complex response may represent substantial breakthroughs in the treatment of various cancers. To show this, two types of $\beta_2$-glycoprotein I/lipid complexes were formed and tested for their therapeutic efficacy in an in vivo cancer therapy model.

5.5.1 Complex Generation $\beta_2$-glycoprotein I was purified from pooled human plasma using previously published procedures (Poltz and Kostner, 1979; Wurm, 1984).

5.5.1.1 Complex I

Microscope slides were coated with 0.9% agarose in 10 mM Tris-HCl pH 7.4 to yield a punch hole volume of 20 μL. The center holes were filled $\beta_2$GPI (300 μg/ml) and the surrounding wells with sonicated small lipid vesicles composed of phosphatidylserine/phosphatidylcholine (50/50). The plates were developed for 24 h and unbound protein and lipid was removed by washing for 24 h in the same buffer. The precipitates containing the protein/lipid complexes were excised, emulsified with Freund's adjuvant and used as described below.

5.5.1.2 Complex II

Phosphatidylserine/phosphatidylcholine (7/3) was resuspended in 20 mM NaCl to yield a final lipid concentration of 5 mg/mL. The lipid suspension was mixed with an equal volume of $\beta_2$-glycoprotein I (450 µg/mL). The suspension was incubated at 4° C. for 2 h and finally mixed with 0.2 volumes of Provax adjuvant (IDEC Pharmaceuticals, San Diego, Calif.).

5.5.2 Induction of Autoimmunity for Prevention of Cancer Utilizing PS/$\beta_2$-glycoprotein BALB/c mice were immunized two weeks apart with 100 µl of antigen subcutaneously and intradermally. One week later control mice, mice treated with Freund's adjuvant only, and the mice immunized against the PS/$\beta_2$-glycoprotein I complex were challenged by an intravenous injection of 20,000 cultured RENCA cells. The lungs of all were harvested 32 days later. Weight of lungs (Table 5) and the number of individual tumor nodules (Table 6) were recorded.

TABLE 5

INHIBITION OF THE FORMATION AND GROWTH OF MURINE RENAL CELL ADENOCARCINOMA (RENCA) IN THE LUNGS OF SYNGENEIC BALB/c MICE AFTER IMMUNIZATION AGAINST PS-$\beta_2$-GLYCOPROTEIN 1 COMPLEX
Lung Weights (mg)

| Control | Adjuvant Alone | Adjuvant $\beta_2$-glycoprotein Complex |
|---|---|---|
| 404 | 427 | 268 |
| 356 | 349 | 241 |
| 349 | 316 | 220 |
| 332 | 284 | 191 |
| 287 | 230 | 185 |
| 262 |  | 177 |
| 229 |  | 158 |
| 209 |  | 150 |
| Xmean = 303 +/− 63 | Xmean 321 +/− 66 | Xmean = 199 +/− 38* |
| Xmedian = 304 | Xmedian = 316 | Xmedian = 188* |

*p < 0.001

TABLE 6

NUMBER OF LUNG TUMOR NODULES

| Control | Adjuvant Alone | Adjuvant $\beta_2$-glycoprotein Complex |
|---|---|---|
| 32 | 35 | 18 |
| 31 | 21 | 15 |
| 24 | 19 | 11 |
| 17 | 18 | 10 |
| 15 | 14 | 10 |
| 14 |  | 8 |
| 12 |  | 5 |
| 11 |  | 3 |
| Xmean = 20 +/− 8 | Xmean = 21 +/− 7 | Xmean = 10 +/− 5 |
| Xmedian = 16 | Xmedian = 19 | Xmedian = 10* |

*p < 0.02

Taken together, these data demonstrate that the generation of an immune response against the disclosed phosphatidylserine conjugates is effective for both the prevention and treatment of cancer and that such treatment and prevention is independent of tumor type and the tumor's physical location in the host. The potential therapeutic and preventive applicability in humans is strongly supported by the fact that very high titers of antibody can be generated in primates.

5.6 Example 5

Animal Models

5.6.1 Materials and Methods

5.6.1.1 Animals

Balb/c mice are purchased from the National Cancer Institute (Frederick, Md.). Animals were maintained in facilities approved by The American Association for Accreditation of Laboratory Animal Care, in accordance with U.S. Department of Agriculture, Department of Health and Human Services, and NIH regulations and standards.

5.6.1.2 Tumor Cell Cultures

Tumor cells are grown as monolayer cultures in Eagle's MEM with 5% fetal bovine serum, vitamins, pyruvate, L-glutamine and non-essential amino acids at 37° C.

5.6.1.3 Immunotherapy with PS-hapten-conjugate

Mice are given subcutaneous immunizations with buffer, KLH-PC, or KLH-PS 7 days and 14 days after administration of the syngeneic tumor cells. Provax adjuvant is used with all immunogens.

5.6.1.4 Tumor Cell Injections

Cell suspensions are prepared by trypsinization. Intravenous injection of about $1.2 \times 10^4$ RENCA cells results in ~10–30 lung tumor nodules in 3–4 weeks. The injection of $5 \times 10^4$ MTB-2 cells into the wall of the bladder results in 100–200 mg tumors in 100% of the mice within 40 days.

5.6.1.5 Therapeutic Efficacy

The end points of therapy are quantitative and allow statistical comparison of antitumor effects and measurement of therapeutic benefit. In the RENCA model, the weight of the lungs and the number of lung tumor nodules (2–4 mm) are compared between experimental groups. In the MTB-2 model, the weights of the bladders and presence of metastasis to the regional lymph nodes are quantified.

5.7 Example 7

Characterization of Autoreactive Immunity

These studies were designed to determine the nature of immune response that is responsible for the PS-dependent killing of syngeneic tumor models. Briefly, the contribution of both cell-mediated and humoral immune mechanisms were examined.

5.7.1 Assay of Macrophage-mediated Tumor Cell Cytotoxicity

Macrophages are obtained from the peritoneum of appropriate groups of mice. $^{125}$I-iododeoxyuridine labeled tumor cells are collected by trypsinization and plated into microtiter plates at $5 \times 10^3$ cells/well (macrophage:target cell ratio= 25:1). As controls, labeled target cells are plated without macrophages. After 72 k, the remaining viable target cells are lysed with detergent. Radiation is measured and the percent of macrophage-mediated cytotoxicity is computed.

5.7.2 Assay of Spleen and Lymph-node Cell Cytotoxicity and Inhibition of Tumor Cell Growth Spleens and lymph nodes are removed from control, tumor-bearing, and immunized, tumor-bearing mice. Cell suspensions are prepared and $10^4$ cells are added to 96-well flat-bottomed microtiter plates with syngeneic target tumor cells ($2 \times 10^5$ lymphocytes/well). Inhibition of tumor growth is measured at 120 h by the hydrolysis of hydroethidine. Cytotoxicity is determined by incubating spleen and lymph node cells with $^{125}$I-target cells described above.

5.73 Data Analysis

Differences in the number of metastases between groups is assessed by the Mann-Whitney test. Significance of cytotoxicity is analyzed by Students t-test.

5.7.4 Assay of APA (Humorasl Response)

Immunized mice are screened for autoreactive antibody by standard sandwich pan anti-mouse Ig. Organs tested included frozen sections of stomach, colon, kidney, liver, lungs, spleen, lymph nodes and muscle. APA titers are assessed by anti-phospholipid antibody assay using standard clinical laboratory (ELISA) technique.

6.0 References

The following literature citations as well as those cited above are incorporated in pertinent part by reference herein for the reasons cited in the above text:

U.S. Pat. No. 3,791,932.
U.S. Pat. No. 3,949,064.
U.S. Pat. No. 4,174,384.
U.S. Pat. No. 4,196,265.
U.S. Pat. No. 4,271,147.
U.S. Pat. No. 4,554,101.
U.S. Pat. No. 4,578,770.
U.S. Pat. No. 4,596,792.
U.S. Pat. No. 4,599,230.
U.S. Pat. No. 4,599,231.
U.S. Pat. No. 4,601,903.
U.S. Pat. No. 4,608,251.
U.S. Pat. No. 4,683,195.
U.S. Pat. No. 4,683,202.
U.S. Pat. No. 4,952,496.
U.S. Pat. No. 5,168,050.
Allen and Choun, *FEBS Lett.*, 223:42–46, 1987.
Alving, *Chem. Phys. Lipids*, 40:303–314, 1986.
Asherson and Cervera, *J. Invest. Dermatol.*, 100:21S, 1993.
Baldwin, O'Reilly, Whitney, Lucy, *Biochim. Biophys. Acta*, 1028:14–20, 1990.
Balet, Clingman, Hagdu, *Biochem. Biophys. Res. Commun.*, 150;561–567, 1988.
Banedji and Alving, *Biochem. Cell. Biol.*, 68:96–101, 1990.
Bate, Taveme, Kwiatkowski, Playfair, *Immunol.*, 79:138–145, 1993.
Becker and Brocker, *Cancer*, 75:2785, 1995.
Becker, Winkler, Klingert, Brocker, *Cancer*, 73:1621, 1994.
Bennett, Gibson, Schwartz, Tait, *Circ. Res.*, 77:1136–1142, 1995.
Bevers, Comfurius, Van Rijn, Hernker, Zwaal, *Eur. J Blochem.*, 122:429–436, 1982.
Bevers, Comfurius, Zwaal, *Biochim. Biophys. Acta*, 736:57–66, 1983.
Bevers, Wiedmer, Comfurius, Zwaal, Sims, *Blood*, 9:380–388, 1992.
Brunner and Richards, *J. Biol Chem.*, 255:3319–3329, 1980.
Comfurius, Bevers, Zwaal, *J. Lipid Res.*, 31:1719–1721, 1990.
Connor, Bucana, Fidler, Schroit, *Proc. Natl. Acad. Sci. USA*, 86:3184, 1989.
Connor, Pak, Schroit, *J. Biol. Chem.*, 269:2399–2404, 1994.
Couvreur et al., *FEBS Lett.*, 84:323–326, 1977.
Couvreur, *Crit. Rev. Ther. Drug Carrier Syst.*, 5:1–20, 1988.
Devaux and Zachowsk *Chem. Phys. Lipids*, 73:107, 1994.
Devaux, *Biochemistry*, 30:1163–1173, 1991.
Diaz, Balasubramanian, Schroit, *Bioconjugate Chem.*, 9:250–254, 1998.
Diaz, Morkowski, Schroit, *Blood*, 87:2956–2961, 1996.
Etemadi, *Biochim. Biophys. Acta*, 604:423–475, 1980.
Fadok, Voelker, Campbell, Cohen, Bratton, Henson, *J. Immunol.*, 148:2207–2216, 1992.
Gabizon and Papahadjopoulos, *Proc. Natl. Acad. Sci. USA*, 85:6949–6953, 1988.
Gaffet, Bettache, Bienvenue, *Eur. J. Cell Biol.*, 67:336–345, 1995.
Galli, Comfurius, Maassen, Hemker, de Baets, van Breda-Vriesman, Barbui, Zwaal, Bevers, *Lancet*, 335:1544–1547, 1990.
Gefter et al., *Somat. Cell Genet.*, 3:231–236, 1977.
Geldwerth, Kuypers, Butikofer, Allary, Lubin, Devaux, *J. Clin. Invest.*, 92:308–314, 1993.
Ghosh and Bacbhawat, *Targeted Diagn. Ther.*, 4:87–103, 1991.
Goding, "Monoclonal Antibodies: Principles and Practice," pp. 60–74. 2nd Edition, Academic Press, Orlando, Fla., 1986.
Gordesky, Marinetti Love, *J. Membr. Biol.*, 20:111–132, 1975.
Grassetti and Murray, *Arch. Blochem. Biophys.*, 119:41–49, 1967.
Harlow, E. and Lane, D. "Antibodies: A Laboratory Manual," Cold Spring Harbor Laboratory, Cold Spring Harbor, N.Y., 1988.
Henry-Michelland et al., *Int. J. Pharm.*, 35:121–127, 1987.
Herrmann and Devaux, *Biochim. Biophys. Acta*, 1027:41–46, 1990.
Herstoff and Bogaars, *Arch. Dermatol.*, 115:856, 1979.
Jue, Lambert, Pierce, Traut, *Biochemistry*, 17:5399–5405, 1978.
Katsuragawa, Rote, Inoue, Narukawa, Kanzaki, Mori, 1995 *Am. J. Obstetr. Gynecol.*, 172:1592–1597, 1995.
Killion and Baker, *Cancer Immunol Immunother.*, 12:111, 1982.
Kohler and Milstein, *Eur. J. Immunol.*, 6:511–519, 1976.
Kuypers, Lewis, Hua, Schott, Discher, Ernst, Lubin, *Blood*, 87:1179–1187, 1996.
Mackworth-Young, *lmmunol. Today*, 11:60, 1990.
Maneta-Peyret, Bessoule, Geffard, Cassagne, *J. Immun. Met.*, 108:123–127, 1988.
Maneta-Peyret, Biron, Previsani, Moreau, Bezian, Cassagne, *Immunol. Lett.*, 35:141–146, 1993.
Maneta-Peyret, Freyburger, Bessoule, Cassagne, *J. Immunol. Meth.*, 122: 155–159, 1989.
McNeil, Simpson, Chesternan, Krilis, *Proc. Natl. Acad Sci. USA*, 87:4120–4124, 1990.
Menon, *Trends Cell Biol.*, 5:355, 1995.
Naldi, Finnazi, Brevi, Cavalieri d'Oro, Locati *Dermatologia*, 184:156, 1992. Nelson, *Pathology*, 9:155, 1977.
OoSting, Derksen, Bobbink, Hackeng, Bouma, de Groot, *Blood*, 81:2618–2625, 1993. Pierotti and Colnaghi *J. Natl. Cancer Inst.*, 55:945, 1975.
Poltz and Kostner, *FEBS Lett.*, 102:183–186, 1979.
Rauch and Janoff, *Proc. Natl. Acad. Sci. USA*, 87:4112–4114, 1990.
Rauch, Tannenbaum, Tannenbaum, Ramelson, Cullis, Tilcock, Hope, Janoff, *J. Biol. Chem.*, 262:9672–9677, 1986.
Regen, Yamaguchi, Samuel, Singh, *J. Am. Chem. Soc.*, 105:6354–6355, 1983. "Remington's Pharmaceutical Sciences" 15 Edition, pages 1035–1038 and 1570 and 1580.
Riddles, Blakely, Zerner, *Meth. Enzymol.*, 91:49–60, 1983.
Rosenberg and Rogentine, *Nature*, 239:203, 1972.
Rosing, Tans, Govers-Riemslag, Zwaal, Hemker, *J. Biol. Chem.*, 255:274–283, 1980.
Rosing, Vanrijn, Bevers, Van Dieijen, Comfurius, Zwaal, *Blood*, 65:319–322, 1985.
Rote, Chang, Katsuragawa, Ng, Lynden, Mori, *Am. J. Rep. Immunol.*, 33:114–121, 1995.
Rote, Ng, DostaI-Johnson, Nicholson, Siekman, *Clin. Immunol. Immunopathol.*, 66:193–200, 1993.
Roubey, *Blood*, 84:2854–2867, 1994.

Sambrano and Steinberg, *Proc. Natl. Acad. Sci. USA*, 92:1396–1400, 1995.
Samuel, Singh, Yamaguchi, Regen, *J. Am. Chem. Soc.*, 107:42–47, 1985.
Schick, Kurica, Chacko, *J. Clin. Invest.*, 57:1221–1226, 1976.
Schousboe, *Biochim. Biophys. Acta*, 579:396–408, 1979.
Schroit and Madsen, *Biochemistry*, 22:3617–3623, 1983.
Schroit and Zwaal, *Biochim. Biophys. Acta*, 1071:313–329, 1991.
Sims, Wiedmer, Esmon, Weiss, Shattil, *J. Biol. Chem.*, 264:17049–17057, 1989.
Tait and Gibson, *J. Lab. Clin. Med.*, 123:741–748, 1994.
Tamamura, Hashimoto, Hara, *Jpn. J. Exp. Med.*, 41:31–38, 1971.
Thiagarajan and Tait, J. Biol. Chem., 265:17420–17423, 1990.
Umeda, Igarashi, Nam, Inoue, Immunol., 143:2273–2279, 1989.
Utsugi, Schroit, Connor, Bucana, Fidler, *Cancer Res.*, 51:3062, 1991.
Van Dieijen, Tans, Rosing, Hemker, *J. Biol. Chem.*, 256:3433–3442, 1981.
Verhoven, Schlegel, Williamson, *J. Exp. Med.*, 182:1597–1601, 1995.
Verkleij, Zwaal, Roelofsen, et al., *Biochim. Biophys. Acta*, 323:178, 1973.
Vermes, Haanen, Steffens-Nakken, Reutelingsperger, *J. Immunol. Meth.*, 184:39–51, 1995.
Wurm, *Int. J. Biochem.*, 16:511–515, 1984.
Zwaal and Schroit, *Blood*, 89:1121–1132, 1997.
Zwaal, Roelofsen, Comfurius, et al., *Biochim. Biophys. Acta*, 406:83, 1975.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are described in the claims below.

What is claimed is:

1. A method of making an antibody that specifically binds to phosphatidylserine, said method comprising administering to an animal a pharmaceutical composition comprising an immunologically effective amount of a phosphatidylserine/polypeptide conjugate composition, wherein the phosphatidylserine is covalently coupled to the volyelptide.

2. The method of claim 1, wherein a the pharmaceutical composition comprises a phosphatidylserine/BSA, phosphatidylserine/KLH, phosphatidylserine/BGG, or phosphatidylserine/$\beta_2$-glycoprotein I conjugate.

3. The method of claim 2, wherein said polypeptide is $\beta_2$-glycoprotein I.

4. The method of claim 1, wherein the antibody is linked to a detectable label.

5. The method of claim 4, wherein the antibody is linked to a radioactive label, a fluorogernic label, a nuclear magnetic spin resonance label, biotin or an enzyme that generates a detectable product upon contact with a chromogenic substrate.

6. The method of claim 4, wherein the antibody is linked to an alkaline phosphatase, hydrogen peroxidase or glucose oxidase enzyme.

7. The method of claim 1, wherein the antibody is a monoclonal antibody.

8. A method of making an antibody that specifically binds to phosphatidylserine, said method comprising administering to an animal a pharmaceutical composition comprising an immunologically effective amount of a phosphatidylserine/polypeptide conjugate composition, wherein the phosphatidylserine/polypeptide conjugate composition is not a phosphatidylserine/KLH conjugate composition, and wherein the phosphatidylserine is covalently coupled to the polypeptide.

9. The method of claim 8, wherein the pharmaceutical composition comprises a phosphatidylserine/BSA, phosphatidylserine/BGG, or phosphatidylserine/$\beta_2$-glycoprotein I conjugate.

10. The method of claim 9, wherein said polypeptide is $\beta_2$-glycoprotein I.

11. The method of claim 8, wherein the antibody is linked to a detectable label.

12. The method of claim 11, wherein the antibody is linked to a radioactive label, a fluorogenic label, a nuclear magnetic spin resonance label, biotin or an enzyme that generates a detectable product upon contact with a chromogenic substrate.

13. The method of claim 11, wherein the antibody is linked to an alkaline phosphatase, hydrogen peroxidase or glucose oxidase enzyme.

14. The method of claim 8, wherein the antibody is a monoclonal antibody.

15. A method of making a monoclonal antibody that specifically binds to phosphatidylserine, said method comprising administering to an animal a pharmaceutical composition comprising an immunologically effective amount of a phosphatidylserine/polypeptide conjugate composition, wherein the phosphatidylserine is covalently coupled to the polypeptide.

16. The method of claim 15, wherein the pharmaceutical composition comprises a phosphatidylserine/BSA, phosphatidylserine/BGG, or phosphatidylserine/$\beta_2$-glycoprotein I conjugate.

17. The method of claim 16, wherein said polypeptide is $\beta_2$-glycoprotein I.

18. The method of claim 15, wherein the antibody is linked to a detectable label.

19. The method of claim 18, wherein the antibody is linked to a radioactive label, a fluorogenic label, a nuclear magnetic spin resonance label, biotin or an enzyme that generates a detectable product upon contact with a chromogenic substrate.

20. The method of claim 18, wherein the antibody is linked to an alkaline phosphatase, hydrogen peroxidase or glucose oxidase enzyme.

* * * * *

UNITED STATES PATENT AND TRADEMARK OFFICE
CERTIFICATE OF CORRECTION

PATENT NO. : 6,806,354 B2  Page 1 of 1
DATED : October 19, 2004
INVENTOR(S) : Schroit, Alan J.

It is certified that error appears in the above-identified patent and that said Letters Patent is hereby corrected as shown below:

Column 33,
Line 59, delete "volyelptide" and insert -- polypeptide --.

Column 34,
Line 4, delete "fluorogernic" and insert -- fluorogenic --.

Signed and Sealed this

Tenth Day of May, 2005

JON W. DUDAS
*Director of the United States Patent and Trademark Office*